(12) United States Patent
de Beuckeleer

(10) Patent No.: US 8,952,142 B2
(45) Date of Patent: Feb. 10, 2015

(54) ELITE EVENT A5547-127 AND METHODS AND KITS FOR IDENTIFYING SUCH EVENT IN BIOLOGICAL SAMPLES

(75) Inventor: Marc de Beuckeleer, Zwijnaarde (BE)

(73) Assignee: Bayer Cropscience N.V., Diegem (BE)

(*) Notice: Subject to any disclaimer, the term of this patent is extended or adjusted under 35 U.S.C. 154(b) by 0 days.

(21) Appl. No.: 13/198,639

(22) Filed: Aug. 4, 2011

(65) Prior Publication Data

US 2012/0117693 A1    May 10, 2012

Related U.S. Application Data

(62) Division of application No. 11/911,167, filed as application No. PCT/EP2006/003455 on Apr. 4, 2006, now Pat. No. 8,017,756.

(60) Provisional application No. 60/670,414, filed on Apr. 12, 2005.

(30) Foreign Application Priority Data

Apr. 11, 2005    (EP) .................................... 05075846

(51) Int. Cl.
*C12Q 1/68*    (2006.01)
*C12N 15/82*    (2006.01)

(52) U.S. Cl.
CPC .......... *C12N 15/8277* (2013.01); *C12Q 1/6895* (2013.01)
USPC .......................................... 536/23.1; 435/6.1

(58) Field of Classification Search
None
See application file for complete search history.

(56) References Cited

U.S. PATENT DOCUMENTS

| | | | |
|---|---|---|---|
| 5,659,113 A | 8/1997 | Rhodes | |
| 5,824,850 A | 10/1998 | Rhodes et al. | |
| 5,834,252 A | 11/1998 | Stemmer et al. | |
| 5,849,482 A * | 12/1998 | Meyer et al. | 435/6.12 |
| 6,177,617 B1 | 1/2001 | Matson et al. | |
| 6,376,754 B1 | 4/2002 | Schillinger et al. | |
| 7,368,527 B2 * | 5/2008 | Rosen et al. | 530/300 |
| 2004/0031072 A1 * | 2/2004 | La Rosa et al. | 800/278 |

OTHER PUBLICATIONS de Beuckeleer (Jul. 1997, Plant Genetic Systems, p. 1-22).*
Lowe et al. (Nucleic Acids Research, 1990, 18(7):1757-1761).*
Accession No. AR053592 (Sep. 29, 1999)"Sequence 16 from patent US 5834252".
Accession No. ADD14982 (May 22, 2003) "Nucleic acid detection by fluorescence energy transfer probe".
Accession No. AY118202 (Jul. 23, 2002) "Simian immunodeficiency virus clone B670_8 envelope glycoprotein gene, partial cds".
De Beuckeleer (1997) "Molecular determination of the number of inserted pat and bla gene copies in liberty link soybean event A5547-127," *Plant Genetic Systems*: 1-22.
Block, et al. (2003) "Validation of different genomic and cloned DNA calibration standards for construct-specific quantification of LibertyLink in rapeseed and by real-time PCR," *European Food Research and Technology* 216(5): 421-427.
Buck (1999) "Design Strategies and Performance of Custom DNA Sequencing Primers," *Biotechniques* (3): 528-536.

(Continued)

*Primary Examiner* — Stephanie K Mummert
(74) *Attorney, Agent, or Firm* — Hunton & Williams LLP

(57) ABSTRACT

Tools are provided which allow rapid and unequivocal identification of elite event A5547-127 in biological samples.

17 Claims, 2 Drawing Sheets

(56) References Cited

OTHER PUBLICATIONS

De Block, et al. (1987) "Engineering herbicide resistance in plants by expression of a detoxifying enzyme," *The Embo Journal* 6(9): 2513-2518.

Edwards, et al. (1991) "A simple and rapid method for the preparation of plant genomic DNA for PCR analysis," *Nucleic Acid Res.* 19(6): 1349.

Food Standards Australia New Zealand (FSANZ) (2004).

Hurburgh (2000) "The GMO Controversy and Grain Handling for 2000," *GMO & Grain* 1-9.

Liu et al. (1995) "Efficient isolation and mapping of *Arabidopsis thaliana* T-DNA insert junctions by thermal asymmetric interlaced PCR," *The Plant Journal* 8(3): 457-463.

Lowe et al. (1990) "A Computer Program for Selection of Oligonucleotide Primers for Polmerase Chain Reactions," *Nucleic Acids Research* 18(7): 1757-1761.

Rott, et al. (2004) "Detection and quantification of roundup ready soy in foods by conventional and real-time polymerase chain reaction," *Journal of Agricultural and Food Chemistry* 52(16): 5223-5232.

Wilbur and Lipman (1983) "Rapid similarity searches of nucleic acid and protein data banks," *Proc. Natl. Acad. Sci.* 80: 726-730.

International Search Report for International Patent Application No. PCT/EP2006/003455, mailed Nov. 20, 2006.

Written Opinion for International Patent Application No. PCT/EP2006/003455, mailed Nov. 20, 2006.

* cited by examiner

SEQUENCE LISTING

```
<160> NUMBER OF SEQ ID NOS: 19

<210> SEQ ID NO 1
<211> LENGTH: 810
<212> TYPE: DNA
<213> ORGANISM: Artificial Sequence
<220> FEATURE:
<223> OTHER INFORMATION: nucleotide sequence comprising a 5' flanking
      region of A5547-127
<220> FEATURE:
<221> NAME/KEY: misc_feature
<222> LOCATION: (1)..(311)
<223> OTHER INFORMATION: 5' flanking sequence
<220> FEATURE:
<221> NAME/KEY: misc_feature
<222> LOCATION: (312)..(810)
<223> OTHER INFORMATION: inserted DNA sequence
```

<400> SEQUENCE: 1

```
gtcatcgtcg tcgcgctgga gttcttgtgg tgccgctggt cgcactggag tttgggtgtt    60
gttgttcatg cttgcgctgc taatcccctt ttgtatgcga aaatcgggtt tgggtcgggt   120
cgggtcagcc caacacgacc taatttgtgt tacgaaaatt tcaacaaaaa aaaaaagtta   180
tcttccgcca ttatcgccat tccgccacga tcattaaggc tatggcggcc gcaatggcgc   240
cgccatatga aacccgcaat gccatcgcta tttggtggca tttttccaaa aacccgcaat   300
gtcataccgt catcgttgtc agaagtaagt tggccgcagt gttatcactc atggttatgg   360
cagcactgca taattctctt actgtcatgc catccgtaag atgcttttct gtgactggtg   420
agtactcaac caagtcattc tgagaatagt gtatgcggcg accgagttgc tcttgcccgg   480
cgtcaatacg ggataatacc cgccacata gcagaacttt aaaagtgctc atcattggaa   540
aacgttcttc ggggcgaaaa ctctcaagga tcttaccgct gttgagatcc agttcgatgt   600
aacccactcg tgcacccaac tgatcttcag catcttttac tttcaccagc gtttctgggt   660
gagcaaaaac aggaaggcaa atgccgcaa aaaagggaat aacgccaggg ttttcccagt   720
cacgacgttg taaaacgacg gccagtgaat tcccatggag tcaaagattc aaatagagga   780
cctaacagaa ctcgccgtaa agactggcga                                    810
```

<210> SEQ ID NO 2
<211> LENGTH: 1880
<212> TYPE: DNA
<213> ORGANISM: Artificial Sequence
<220> FEATURE:
<223> OTHER INFORMATION: nucleotide sequence comprising the 3' flanking
      region of A5547-127
<220> FEATURE:
<221> NAME/KEY: misc_feature
<222> LOCATION: (1)..(509)
<223> OTHER INFORMATION: inserted DNA sequences
<220> FEATURE:
<221> NAME/KEY: misc_feature
<222> LOCATION: (510)..(1880)
<223> OTHER INFORMATION: 3' flanking DNA sequences

<400> SEQUENCE: 2

```
cttttaaatt aaaaatgaag ttttaaatca atctaaagta tatatgagta aacttggtct    60
gacagttacc aatgcttaat cagtgaggca cctatctcag cgatctgtct atttcgttca   120
tccatagttg cctgactccc cgtcgtgtag ataactacga tacgggaggg cttaccatct   180
ggccccagtg ctgcaatgat accgcgagac ccacgctcac cggctccaga tttatcagca   240
ataaaccagc cagccggaag ggccgagcgc agaagtggtc ctgcaacttt atccgcctcc   300
atccagtcta ttaattgttg ccgggaagct agagtaagta gttcgccagt taatagtttg   360
cgcaacgttg ttgccattgc tacaggcatc gtggtgtcac gctcgtcgtt tggtatggct   420
tcattcagct ccggttccca acgatcaagg cgagttacat gatcccccat gttgtgcaaa   480
aaagcggtta gctccttcgg tcctccgatg gcaccgccat aaccacaatt taacaacttt   540
ataaatgact tagtatatta gcaatttatc ttgtcacatg cacatatttt ataactataa   600
taggagtttg agtttaaatg atgtaatgaa ttttggattg catgttgttt tgtactatat   660
tggtagcttt ttccaatgaa gtgttaaatt tgtattttc atattcaggg tcacgtttga   720
ccttctctag tcactgccct aattaagccc tttctcttgc actcttgatg cttacttaac   780
ctgggcatca ggcatatgta atgttatcaa tcaaactatc acgttcatg catttattaa   840
tcttcattga tgcccttgtc tcgctcttgc cccttttttcc aatttatgct tcaaatctttt  900
```

```
gacatgttcc atgtccttat tccttttctc tgtaactgtt cattttcgtt atgaaccatg    960
aagataaact actattgtta aagtctcggt tcaaatttaa cttttctgct tttccccata    1020
taattgaata agacttggtc gtggttgttc tcattgcata tacctttatt atatgcatag    1080
aagtgatttt tttgcctaac ttgtacattt ttttatggca gtgatganga tgtagagagg    1140
cttatcgagc ttgtgaaggg aatttcttgc aagattaatc taatctcatt caatccgcac    1200
agtggatcat tcttcaaacc aaccaaatat gaaaggatga ttgaattccg aaatacattg    1260
gctggggcag gattgatagt atttttaaga cttagtagag gtgatgatca attggcttcc    1320
tgtggtcaat tgggtaagcc tggcaccatt caagctccat tcttcgtgt accagagcaa     1380 ttccaaatgg caattggaag ttcaacttga ttctttgtgg aggttctgtg gcaaattgat    1440
cttacagtta ttaacgaaga attatatagg acacttgtgg tggggtagc tagggatgac     1500 ttcatactga caatgcaaga ccaagagcta aattagggg atgtctgtct gttttcatat     1560
tgtacttttc cattttacag ttaattgata tattttttt tattaatgtg acggatccag     1620
attacttact ggctaagaaa taagaaataa aaatgattta aatatatttt tagtcgaagt    1680
ctgtattttt tagtttccca aattaaaatt tgcattttt aatctctcat ttataaaatg     1740
cctttttaag ttcttcttag ctgattttg gcaacttgga tgcacaatgt gcaactatcg     1800
taacaatatt tttcttgaaa tttaaagaga ctaaaatata tgttttacca taacactcat    1860
gttagtaaaa ccattatttg                                                1880

<210> SEQ ID NO 3
<211> LENGTH: 21
<212> TYPE: DNA
<213> ORGANISM: Artificial Sequence
<220> FEATURE:
<223> OTHER INFORMATION: primer HCA150

<400> SEQUENCE: 3
tcgtcgcgct ggagttcttg t                                              21

<210> SEQ ID NO 4
<211> LENGTH: 21
<212> TYPE: DNA
<213> ORGANISM: Artificial Sequence
<220> FEATURE:
<223> OTHER INFORMATION: primer DPA013

<400> SEQUENCE: 4
tcatgcttgc gctgctaatc c                                              21

<210> SEQ ID NO 5
<211> LENGTH: 20
<212> TYPE: DNA
<213> ORGANISM: Artificial Sequence
<220> FEATURE:
<223> OTHER INFORMATION: primer DPA228

<400> SEQUENCE: 5
acccgcaatg tcataccgtc                                                20

<210> SEQ ID NO 6
<211> LENGTH: 21
<212> TYPE: DNA
<213> ORGANISM: Artificial Sequence
<220> FEATURE:
<223> OTHER INFORMATION: primer KVM173
```

<400> SEQUENCE: 6
tgctgccata accatgagtg a                                              21

<210> SEQ ID NO 7
<211> LENGTH: 21
<212> TYPE: DNA
<213> ORGANISM: Artificial Sequence
<220> FEATURE:
<223> OTHER INFORMATION: primer YTP228

<400> SEQUENCE: 7
atcttacgga tggcatgaca g                                              21

<210> SEQ ID NO 8
<211> LENGTH: 27
<212> TYPE: DNA
<213> ORGANISM: Artificial Sequence
<220> FEATURE:
<223> OTHER INFORMATION: primer YTP220

<400> SEQUENCE: 8
aactggatct caacagcggt aagatcc                                        27

<210> SEQ ID NO 9
<211> LENGTH: 21
<212> TYPE: DNA
<213> ORGANISM: Artificial Sequence
<220> FEATURE:
<223> OTHER INFORMATION: primer DPA024

<400> SEQUENCE: 9
gttttacaac gtcgtgactg g                                              21

<210> SEQ ID NO 10
<211> LENGTH: 21
<212> TYPE: DNA
<213> ORGANISM: Artificial Sequence
<220> FEATURE:
<223> OTHER INFORMATION: PRIMER YTP245

<400> SEQUENCE: 10
ggcgagttct gttaggtcct c                                              21

<210> SEQ ID NO 11
<211> LENGTH: 21
<212> TYPE: DNA
<213> ORGANISM: Artificial Sequence
<220> FEATURE:
<223> OTHER INFORMATION: primer YTP170

<400> SEQUENCE: 11
agtgaggcac ctatctcagc g                                              21

<210> SEQ ID NO 12
<211> LENGTH: 21
<212> TYPE: DNA
<213> ORGANISM: Artificial Sequence
<220> FEATURE:
<223> OTHER INFORMATION: primer YTP227

<400> SEQUENCE: 12
agcaataaac cagccagccg g                                              21

<210> SEQ ID NO 13
<211> LENGTH: 21

```
<212> TYPE: DNA
<213> ORGANISM: Artificial Sequence
<220> FEATURE:
<223> OTHER INFORMATION: primer MDB688

<400> SEQUENCE: 13
tgctacaggc atcgtggtgt c                                              21

<210> SEQ ID NO 14
<211> LENGTH: 21
<212> TYPE: DNA
<213> ORGANISM: Artificial Sequence
<220> FEATURE:
<223> OTHER INFORMATION: primer KVM175

<400> SEQUENCE: 14
gcaaaaaagc ggttagctcc t                                              21

<210> SEQ ID NO 15
<211> LENGTH: 21
<212> TYPE: DNA
<213> ORGANISM: Artificial Sequence
<220> FEATURE:
<223> OTHER INFORMATION: primer MDB687

<400> SEQUENCE: 15
tgtggttatg gcggtgccat c                                              21

<210> SEQ ID NO 16
<211> LENGTH: 20
<212> TYPE: DNA
<213> ORGANISM: Artificial Sequence
<220> FEATURE:
<223> OTHER INFORMATION: primer SMO022

<400> SEQUENCE: 16
aaggtcaaac gtgaccctga                                                20

<210> SEQ ID NO 17
<211> LENGTH: 20
<212> TYPE: DNA
<213> ORGANISM: Artificial Sequence
<220> FEATURE:
<223> OTHER INFORMATION: primer SMO024

<400> SEQUENCE: 17
gaagaatgat ccactgtgcg                                                20

<210> SEQ ID NO 18
<211> LENGTH: 21
<212> TYPE: DNA
<213> ORGANISM: Artificial Sequence
<220> FEATURE:
<223> OTHER INFORMATION: primer 1 for amplification of endogenous
      control fragment

<400> SEQUENCE: 18
tgtggttatg gcggtgccat c                                              21

<210> SEQ ID NO 19
<211> LENGTH: 21
<212> TYPE: DNA
<213> ORGANISM: Artificial Sequence
```

```
<220> FEATURE:
<223> OTHER INFORMATION: primer 2 for amplification of endogenous
      control fragment

<400> SEQUENCE: 19
tgctacaggc atcgtggtgt c                                              21
```

US 8,952,142 B2

ELITE EVENT A5547-127 AND METHODS AND KITS FOR IDENTIFYING SUCH EVENT IN BIOLOGICAL SAMPLES

CROSS-REFERENCE TO RELATED APPLICATIONS

This application is a divisional of U.S. patent application Ser. No. 11/911,167, filed Oct. 10, 2007, now U.S. Pat. No. 8,017,756, which is the U.S. National Stage filing of International Application No. PCT/EP2006/003455, filed Apr. 4, 2006, which claims priority to EP 05075846.5, filed Apr. 11, 2005, U.S. Provisional Patent Application No. 60/670,414, filed Apr. 12, 2005, the disclosures of each of which are hereby incorporated by reference.

FIELD OF THE INVENTION

This invention pertains to methods and kits for identifying in biological samples the presence of plant material comprising specifically transformation event A5547-127, as well as transgenic soybean plants, plant material and seeds containing such event. The soybean plants of the invention combine the herbicide tolerant phenotype with an agronomic performance, genetic stability and adaptability to different genetic backgrounds equivalent to the non-transformed soybean line in the absence of weed pressure.

BACKGROUND OF THE INVENTION

The phenotypic expression of a transgene in a plant is determined both by the structure of the gene itself and by its location in the plant genome. At the same time the presence of the transgene (in a foreign DNA) at different locations in the genome will influence the overall phenotype of the plant in different ways. The agronomically or industrially successful introduction of a commercially interesting trait in a plant by genetic manipulation can be a lengthy procedure dependent on different factors. The actual transformation and regeneration of genetically transformed plants are only the first in a series of selection steps, which include extensive genetic characterization, breeding, and evaluation in field trials, eventually leading to the selection of an elite event.

The unequivocal identification of an elite event is becoming increasingly important in view of discussions on Novel Food/Feed, segregation of GMO and non-GMO products and the identification of proprietary material. Ideally, such identification method is both quick and simple, without the need for an extensive laboratory set-up. Furthermore, the method should provide results that allow unequivocal determination of the elite event without expert interpretation, but which hold up under expert scrutiny if necessary.

A5547-127 was selected as an elite event in the development of soybean (Glycine max L.) resistant to the herbicide Liberty®, by transformation of soybean with a plasmid comprising the synthetic pat gene encoding tolerance to phosphinothricin and may be commercially sold as Liberty Link® soybean. The tools for use in simple and unequivocal methods for identification elite event A5547-127 in biological samples are described herein.

SUMMARY OF THE INVENTION

The present invention relates to methods for identifying elite event A5547-127 in biological samples, which methods are based on primers or probes which specifically recognize the 5' and/or 3' flanking sequence of A5547-127.

More specifically, the invention relates to a method comprising of amplifying a sequence of a nucleic acid present in biological samples, using a polymerase chain reaction with at least two primers, one of which recognizes the 5' or 3' flanking region of A5547-127, the other which recognizes a sequence within the foreign DNA, preferably to obtain a DNA fragment of between 100 and 500 bp. The primers may recognize a sequence within the 5' flanking region of A5547-127 (SEQ ID No. 1, from position 1 to position 311) or within the 3' flanking region of A5547-127 (complement of SEQ ID No 2 from position 510 to position 1880) and a sequence within the foreign DNA (complement of SEQ ID No 1 from position 312 to 810 or SEQ ID No 2 from position 1 to position 510), respectively. The primer recognizing the 5' flanking region may comprise the nucleotide sequence of SEQ ID No. 15 and the primer recognizing a sequence within the foreign DNA may comprise the nucleotide sequence of SEQ ID No. 13 described herein.

The present invention more specifically relates to a method for identifying elite event A5547-127 in biological samples, which method comprises amplifying a sequence of a nucleic acid present in a biological sample, using a polymerase chain reaction with two primers having the nucleotide sequence of SEQ ID No. 15 and SEQ ID No. 13 respectively, to obtain a DNA fragment of about 151 bp.

The present invention further relates to the specific flanking sequences of A5547-127 described herein, which can be used to develop specific identification methods for A5547-127 in biological samples. More particularly, the invention relates to the 5' and or 3' flanking regions of A5547-127 which can be used for the development of specific primers and probes as further described herein. The invention further relates to identification methods for the presence of A5547-127 in biological samples based on the use of such specific primers or probes. Primers may consist of a nucleotide sequence of 17 to about 200 consecutive nucleotides selected from the nucleotide sequence of SEQ ID No 1 from nucleotide 1 to nucleotide 311 or the complement of the nucleotide sequence of SEQ ID 2 from nucleotide 510 to nucleotide 1880) combined with primers consisting of a nucleotide sequence of 17 to about 200 consecutive nucleotides selected from the complement of the nucleotide sequence of SEQ ID No 1 from nucleotide 312 to nucleotide 810 or the nucleotide sequence of SEQ ID No 2 from nucleotide 1 to nucleotide 510. Primers may also comprise these nucleotide sequences located at their extreme 3' end, and further comprise unrelated sequences or sequences derived from the mentioned nucleotide sequences, but comprising mismatches.

The invention further relates to kits for identifying elite event A5547-127 in biological samples, said kits comprising at least one primer or probe which specifically recognizes the 5' or 3' flanking region of A5547-127.

The kit of the invention may comprise, in addition to a primer which specifically recognizes the 5' or 3' flanking region of A5547-127, a second primer which specifically recognizes a sequence within the foreign DNA of A5547-127, for use in a PCR identification protocol. Preferably, the kit of the invention comprises two specific primers, one of which recognizes a sequence within the 5' flanking region of A5547-127, and the other which recognizes a sequence within the foreign DNA. Especially The primer recognizing the 5' flanking region may comprises the nucleotide sequence of SEQ ID No. 14 and the primer recognizing the transgene may comprises the nucleotide sequence of SEQ ID No. 13 or any other primer as described herein.

The invention further relates to a kit for identifying elite event A5547-127 in biological samples, said kit comprising the PCR primers having the nucleotide sequence of SEQ ID No. 13 and SEQ ID No. 15 for use in the A5547-127 PCR identification protocol described herein.

The invention also relates to a kit for identifying elite event A5547-127 in biological samples, which kit comprises a specific probe having a sequence which corresponds (or is complementary to) a sequence having between 80% and 100% sequence identity with a specific region of A5547-127. Preferably the sequence of the probe corresponds to a specific region comprising part of the 5' or 3' flanking region of A5547-127. Most preferably the specific probe has (or is complementary to) a sequence having between 80% and 100% sequence identity to the sequence between nucleotide 360 and 460 of SEQ ID No. 1 or the sequence between nucleotide 460 and 560 of SEQ ID No 2.

The methods and kits encompassed by the present invention can be used for different purposes such as, but not limited to the following: to identify the presence or absence of A5547-127 in plants, plant material or in products such as, but not limited to food or feed products (fresh or processed) comprising or derived from plant material; additionally or alternatively, the methods and kits of the present invention can be used to identify transgenic plant material for purposes of segregation between transgenic and non-transgenic material; additionally or alternatively, the methods and kits of the present invention can be used to determine the quality (i.e. percentage pure material) of plant material comprising A5547-127.

The invention further relates to the 5' and/or 3' flanking regions of A5547-127 as well as to the specific primers and probes developed from the 5' and/or 3' flanking sequences of A5547-127.

The invention also relates to soybean plants, parts thereof, cells, seeds and progeny plants comprising elite event A5547-127. Such plants, parts thereof, cells, seeds and progeny plants can be identified using the methods as herein described.

DETAILED DESCRIPTION

The incorporation of a recombinant DNA molecule in the plant genome typically results from transformation of a cell or tissue (or from another genetic manipulation). The particular site of incorporation is either due to "random" integration or is at a predetermined location (if a process of targeted integration is used).

The DNA introduced into the plant genome as a result of transformation of a plant cell or tissue with a recombinant DNA or "transforming DNA", and originating from such transforming DNA is hereinafter referred to as "foreign DNA" comprising one or more "transgenes". "Plant DNA" in the context of the present invention will refer to DNA originating from the plant which is transformed. Plant DNA will usually be found in the same genetic locus in the corresponding wild-type plant. The foreign DNA can be characterized by the location and the configuration at the site of incorporation of the recombinant DNA molecule in the plant genome. The site in the plant genome where a recombinant DNA has been inserted is also referred to as the "insertion site" or "target site". Insertion of the recombinant DNA into the plant genome can be associated with a deletion of plant DNA, referred to as "target site deletion". A "flanking region" or "flanking sequence" as used herein refers to a sequence of at least 20 bp, preferably at least 50 bp, and up to 5000 bp of the plant genome which is located either immediately upstream of and contiguous with or immediately downstream of and contiguous with the foreign DNA. Transformation procedures leading to random integration of the foreign DNA will result in transformants with different flanking regions, which are characteristic and unique for each transformant. When the recombinant DNA is introduced into a plant through traditional crossing, its insertion site in the plant genome, or its flanking regions will generally not be changed. An "insertion region" as used herein refers to the region corresponding to the region of at least 40 bp, preferably at least 100 bp, and up to 10000 bp, encompassed by the sequence which comprises the upstream and/or the downstream flanking region of a foreign DNA in the plant genome. Taking into consideration minor differences due to mutations within a species, an insertion region will retain, upon crossing into a plant of the same species, at least 85%, preferably 90%, more preferably 95%, and most preferably 100% sequence identity with the sequence comprising the upstream and downstream flanking regions of the foreign DNA in the plant originally obtained from transformation.

An event is defined as a (artificial) genetic locus that, as a result of genetic engineering, carries a transgene comprising at least one copy of a gene of interest. The typical allelic states of an event are the presence or absence of the foreign DNA. An event is characterized phenotypically by the expression of the transgene. At the genetic level, an event is part of the genetic makeup of a plant. At the molecular level, an event can be characterized by the restriction map (e.g. as determined by Southern blotting), by the upstream and/or downstream flanking sequences of the transgene, the location of molecular markers and/or the molecular configuration of the transgene. Usually transformation of a plant with a transforming DNA comprising at least one gene of interest leads to a multitude of events, each of which is unique.

An elite event, as used herein, is an event which is selected from a group of events, obtained by transformation with the same transforming DNA or by back-crossing with plants obtained by such transformation, based on the expression and stability of the transgene(s) and its compatibility with optimal agronomic characteristics of the plant comprising it. Thus the criteria for elite event selection are one or more, preferably two or more, advantageously all of the following:
a) That the presence of the foreign DNA does not compromise other desired characteristics of the plant, such as those relating to agronomic performance or commercial value;
b) That the event is characterized by a well defined molecular configuration which is stably inherited and for which appropriate tools for identity control can be developed; c) That the gene(s) of interest show(s) a correct, appropriate and stable spatial and temporal phenotypic expression, both in heterozygous (or hemizygous) and homozygous condition of the event, at a commercially acceptable level in a range of environmental conditions in which the plants carrying the event are likely to be exposed in normal agronomic use.

It is preferred that the foreign DNA is associated with a position in the plant genome that allows easy introgression into desired commercial genetic backgrounds.

The status of an event as an elite event is confirmed by introgression of the elite event in different relevant genetic backgrounds and observing compliance with one, two or all of the criteria e.g. a), b) and c) above.

An "elite event" thus refers to a genetic locus comprising a foreign DNA, which answers to the above-described criteria. A plant, plant material or progeny such as seeds can comprise one or more elite events in its genome.

The tools developed to identify an elite event or the plant, plant material comprising an elite event, or products which comprise plant material comprising the elite event are based on the specific genomic characteristics of the elite event, such as, a specific restriction map of the genomic region comprising the foreign DNA, molecular markers or the sequence of the flanking region(s) of the foreign DNA.

Once one or both of the flanking regions of the foreign DNA have been sequenced, primers and probes can be developed which specifically recognize this (these) sequence(s) in the nucleic acid (DNA or RNA) of a sample by way of a molecular biological technique. For instance a PCR method can be developed to identify the elite event in biological samples (such as samples of plants, plant material or products comprising plant material). Such a PCR is based on at least two specific "primers" one recognizing a sequence within the 5' or 3' flanking region of the elite event and the other recognizing a sequence within the foreign DNA. The primers preferably have a sequence of between 15 and 35 nucleotides which under optimized PCR conditions "specifically recognize" a sequence within the 5' or 3' flanking region of the elite event and the foreign DNA of the elite event respectively, so that a specific fragment ("integration fragment" or discriminating amplicon) is amplified from a nucleic acid sample comprising the elite event. This means that only the targeted integration fragment, and no other sequence in the plant genome or foreign DNA, is amplified under optimized PCR conditions.

PCR primers suitable for the invention may be the following:
  oligonucleotides ranging in length from 17 nt to about 300 nt, comprising a nucleotide sequence of at least 17 consecutive nucleotides, preferably 20 consecutive nucleotides selected from the 5' flanking sequence (SEQ ID No 1 from nucleotide 1 to nucleotide 311) at their 3' end (primers recognizing 5' flanking sequences); or
  oligonucleotides ranging in length from 17 nt to about 300 nt, comprising a nucleotide sequence of at least 17 consecutive nucleotides, preferably 20 consecutive nucleotides, selected from the 3' flanking sequence (complement of SEQ ID No 2 from nucleotide 510 to nucleotide 1880) at their 3' end (primers recognizing 3' flanking sequences); or
  oligonucleotides ranging in length from 17 nt to about 510 nt, comprising a nucleotide sequence of at least 17 consecutive nucleotides, preferably 20 nucleotides selected from the inserted DNA sequences (complement of SEQ ID No 1 from nucleotide 312 to nucleotide 810) at their 3' end (primers recognizing foreign DNA) or
  oligonucleotides ranging in length from 17 nt to about 300 nt, comprising a nucleotide sequence of at least 17 consecutive nucleotides, preferably 20 nucleotides selected from the inserted DNA sequences (SEQ ID No 2 from nucleotide 1 to nucleotide 509)

The primers may of course be longer than the mentioned 17 consecutive nucleotides, and may e.g. be 20, 21, 30, 35, 50, 75, 100, 150, 200 nt long or even longer. The primers may entirely consist of nucleotide sequence selected from the mentioned nucleotide sequences of flanking sequences and foreign DNA sequences. However, the nucleotide sequence of the primers at their 5' end (i.e. outside of the 3'-located 17 consecutive nucleotides) is less critical. Thus, the 5' sequence of the primers may consist of a nucleotide sequence selected from the flanking sequences or foreign DNA, as appropriate, but may contain several (e.g. 1, 2, 5, 10 mismatches). The 5' sequence of the primers may even entirely consist of a nucleotide sequence unrelated to the flanking sequences or foreign DNA, such as e.g. a nucleotide sequence representing restriction enzyme recognition sites. Such unrelated sequences or flanking DNA sequences with mismatches should preferably be not longer than 100, more preferably not longer than 50 or even 25 nucleotides.

Moreover, suitable primers may comprise or consist of a nucleotide sequence at their 3' end spanning the joining region between the plant DNA derived sequences and the foreign DNA sequences (located at nucleotides 311-312 in SEQ ID No 1 and nucleotides 509-510 in SEQ ID No 2) provided the mentioned 3'-located 17 consecutive nucleotides are not derived exclusively from either the foreign DNA or plant-derived sequences in SEQ ID No 1 or 2.

Thus, PCR primers suitable for the invention may also be the following:
  oligonucleotides ranging in length from 17 nt to about 300 nt, comprising a nucleotide sequence of at least 17 consecutive nucleotides, preferably 20 consecutive nucleotides selected SEQ ID No 1 from nucleotide 1 to nucleotide 325) at their 3' end; or oligonucleotides ranging in length from 17 nt to about 300 nt, comprising a nucleotide sequence of at least 17 consecutive nucleotides, preferably 20 consecutive nucleotides, selected from the complement of SEQ ID No 2 from nucleotide 495 to nucleotide 1880) at their 3' end; or
  oligonucleotides ranging in length from 17 nt to about 300 nt, comprising a nucleotide sequence of at least 17 consecutive nucleotides, preferably 20 nucleotides selected from the complement of SEQ ID No 1 from nucleotide 295 to nucleotide 810) at their 3' end or oligonucleotides ranging in length from 17 nt to about 300 nt, comprising a nucleotide sequence of at least 17 consecutive nucleotides, preferably 20 nucleotides selected from SEQ ID No 2 from nucleotide 1 to nucleotide 525).

It will also be immediately clear to the skilled artisan that properly selected PCR primer pairs should also not comprise sequences which are complementary to each other.

For the purpose of the invention, the "complement of a nucleotide sequence represented in SEQ ID No: X" is the nucleotide sequence which can be derived from the represented nucleotide sequence by replacing the nucleotides through their complementary nucleotide according to Chargaff's rules (AOT; GOC) and reading the sequence in the 5' to 3' direction, i.e in opposite direction ^f the re-nresented nucleotide seαuence.

Examples of suitable primers are the oligonucleotide sequences of SEQ ID No 3, SEQ ID No 4, SEQ ID No 5 (5' flanking sequence recognizing primers) SEQ ID No 6, SEQ ID No 7, SEQ ID No 8, SEQ ID No 9, SEQ ID No 10 (foreign DNA recognizing primers for use with the 5' flanking sequence recognizing primers) SEQ ID No 11, SEQ ID No 12, SEQ ID No 13, SEQ ID No 14 (foreign DNA recognizing primers for use with the 3' flanking sequence recognizing primers) SEQ ID No 15, SEQ ID No 16 or SEQ ID No 17 (3' flanking sequence recognizing primers).

Other examples of suitable oligonucleotide primers comprise at their 3' end the following sequences or consist of such sequences:
a. 5' flanking sequence recognizing primers: the nucleotide sequence of SEQ ID No 1 from nucleotide 45 to nucleotide 64—the nucleotide sequence of SEQ ID No 1 from nucleotide 22 to nucleotide 41
  the nucleotide sequence of SEQ ID No 1 from nucleotide 47 to nucleotide 64
  the nucleotide sequence of SEQ ID No 1 from nucleotide 183 to nucleotide 202 the nucleotide sequence of SEQ ID No 1 from nucleotide 184 to nucleotide 203 the nucleotide sequence of SEQ ID No 1 from nucleotide 301 to nucleotide 320—the nucleotide sequence of SEQ ID No 1 from nucleotide 303 to nucleotide 322 the nucleotide sequence of SEQ ID No 1 from nucleotide 306 to nucleotide 325 the nucleotide sequence of SEQ ID No 1 from nucleotide 36 to nucleotide 55 the nucleotide sequence of SEQ ID No 1 from nucleotide 182 to nucleotide 202 the nucleotide sequence of SEQ ID No 1 from nucleotide 183 to nucleotide 203—the nucleotide sequence of SEQ ID No 1 from nucleotide 184 to nucleotide 202 the nucleotide sequence of SEQ ID No 1 from nucleotide 185 to nucleotide 203 the nucleotide sequence of SEQ ID No 1 from nucleotide 185 to nucleotide 204 the nucleotide sequence of SEQ ID No 1 from nucleotide 292 to nucleotide 311 the nucleotide sequence of SEQ ID No 1 from nucleotide 295 to nucleotide 314 the nucleotide sequence of SEQ ID No 1 from nucleotide 307 to nucleotide 325 the nucleotide sequence of SEQ ID No 1 from nucleotide 8 to nucleotide 27—the nucleotide sequence of SEQ ID No 1 from nucleotide 10 to nucleotide 29 the nucleotide sequence of SEQ ID No 1 from nucleotide 11 to nucleotide 30 the nucleotide sequence of SEQ ID No 1 from nucleotide 13 to nucleotide 32 the nucleotide sequence of SEQ ID No 1 from nucleotide 20 to nucleotide 41 the nucleotide sequence of SEQ ID No 1 from nucleotide 35 to nucleotide 54—the nucleotide sequence of SEQ ID No 1 from nucleotide 37 to nucleotide 55 the nucleotide sequence of SEQ ID No 1 from nucleotide 66 to nucleotide 85 the nucleotide sequence of SEQ ID No 1 from nucleotide 67 to nucleotide 86 the nucleotide sequence of SEQ ID No 1 from nucleotide 68 to nucleotide 87 the nucleotide sequence of SEQ ID No 1 from nucleotide 181 to nucleotide 202—the nucleotide sequence of SEQ ID No 1 from nucleotide 182 to nucleotide 203 the nucleotide sequence of SEQ ID No 1 from nucleotide 184 to nucleotide 204 the nucleotide sequence of SEQ ID No 1 from nucleotide 185 to nucleotide 202 the nucleotide sequence of SEQ ID No 1 from nucleotide 186 to nucleotide 204 the nucleotide sequence of SEQ ID No 1 from nucleotide 186 to nucleotide 203—the nucleotide sequence of SEQ ID No 1 from nucleotide 248 to nucleotide 267 the nucleotide sequence of SEQ ID No 1 from nucleotide 249 to nucleotide 268 the nucleotide sequence of SEQ ID No 1 from nucleotide 290 to nucleotide 309 the nucleotide sequence of SEQ ID No 1 from nucleotide 291 to nucleotide 311 the nucleotide sequence of SEQ ID No 1 from nucleotide 293 to nucleotide 311—the nucleotide sequence of SEQ ID No 1 from nucleotide 294 to nucleotide 314 the nucleotide sequence of SEQ ID No 1 from nucleotide 301 to nucleotide 322 the nucleotide sequence of SEQ ID No 1 from nucleotide 303 to nucleotide 320 the nucleotide sequence of SEQ ID No 1 from nucleotide 305 to nucleotide 322 the nucleotide sequence of SEQ ID No 1 from nucleotide 308 to nucleotide 325—the nucleotide sequence of SEQ ID No 1 from nucleotide 11 to nucleotide 29 the nucleotide sequence of SEQ ID No 1 from nucleotide 36 to nucleotide 54 the nucleotide sequence of SEQ ID No 1 from nucleotide 41 to nucleotide 61—the nucleotide sequence of SEQ ID No 1 from nucleotide 43 to nucleotide 64 the nucleotide sequence of SEQ ID No 1 from nucleotide 66 to nucleotide 86 the nucleotide sequence of SEQ ID No 1 from nucleotide 67 to nucleotide 85—the nucleotide sequence of SEQ ID No 1 from nucleotide 67 to nucleotide 87 the nucleotide sequence of SEQ ID No 1 from nucleotide 68 to nucleotide 86 the nucleotide sequence of SEQ ID No 1 from nucleotide 69 to nucleotide 87 the nucleotide sequence of SEQ ID No 1 from nucleotide 180 to nucleotide 197 the nucleotide sequence of SEQ ID No 1 from nucleotide 183 to nucleotide 204—the nucleotide sequence of SEQ ID No 1 from nucleotide 187 to nucleotide 204 the nucleotide sequence of SEQ ID No 1 from nucleotide 200 to nucleotide 219 the nucleotide sequence of SEQ ID No 1 from nucleotide 246 to nucleotide 263 the nucleotide sequence of SEQ ID No 1 from nucleotide 247 to nucleotide 267 the nucleotide sequence of SEQ ID No 1 from nucleotide 248 to nucleotide 268—the nucleotide sequence of SEQ ID No 1 from nucleotide 249 to nucleotide 267 the nucleotide sequence of SEQ ID No 1 from nucleotide 250 to nucleotide 268 the nucleotide sequence of SEQ ID No 1 from nucleotide 290 to nucleotide 311 the nucleotide sequence of SEQ ID No 1 from nucleotide 291 to nucleotide 308 the nucleotide sequence of SEQ ID No 1 from nucleotide 291 to nucleotide 309—the nucleotide sequence of SEQ ID No 1 from nucleotide 293 to nucleotide 214 the nucleotide sequence of SEQ ID No 1 from nucleotide 8 to nucleotide 29 the nucleotide sequence of SEQ ID No 1 from nucleotide 11 to nucleotide 32 the nucleotide sequence of SEQ ID No 1 from nucleotide 37 to nucleotide 54 the nucleotide sequence of SEQ ID No 1 from nucleotide 40 to nucleotide 61—the nucleotide sequence of SEQ ID No 1 from nucleotide 64 to nucleotide 85 the nucleotide sequence of SEQ ID No 1 from nucleotide 65 to nucleotide 86 the nucleotide sequence of SEQ ID No 1 from nucleotide 66 to nucleotide 87 the nucleotide sequence of SEQ ID No 1 from nucleotide 68 to nucleotide 85 the nucleotide sequence of SEQ ID No 1 from nucleotide 69 to nucleotide 86—the nucleotide sequence of SEQ ID No 1 from nucleotide 197 to nucleotide 218 the nucleotide sequence of SEQ ID No 1 from nucleotide 201 to nucleotide 219 the nucleotide sequence of SEQ ID No 1 from nucleotide 201 to nucleotide 218—the nucleotide sequence of SEQ ID No 1 from nucleotide 234 to nucleotide 253 the nucleotide sequence of SEQ ID No 1 from nucleotide 244 to nucleotide 263 the nucleotide sequence of SEQ ID No 1 from nucleotide 246 to nucleotide 267 the nucleotide sequence of SEQ ID No 1 from nucleotide 247 to nucleotide 268—the nucleotide sequence of SEQ ID No 1 from nucleotide 250 to nucleotide 267 the nucleotide sequence of SEQ ID No 1 from nucleotide 292 to nucleotide 309 the nucleotide sequence of SEQ ID No 1 from nucleotide 198 to nucleotide 219 the nucleotide sequence of SEQ ID No 1 from nucleotide 202 to nucleotide 219 the nucleotide sequence of SEQ ID No 1 from nucleotide 233 to nucleotide 253—the nucleotide sequence of SEQ ID No 1 from nucleotide 235 to nucleotide 254 the nucleotide sequence of SEQ ID No 1 from nucleotide 235 to nucleotide 253
the nucleotide sequence of SEQ ID No 1 from nucleotide 243 to nucleotide 263
the nucleotide sequence of SEQ ID No 1 from nucleotide 232 to nucleotide 253
the nucleotide sequence of SEQ ID No 1 from nucleotide 234 to nucleotide 254—the nucleotide sequence of SEQ ID No 1 from nucleotide 242 to nucleotide 263
the nucleotide sequence of SEQ ID No 1 from nucleotide 233 to nucleotide 254
the nucleotide sequence of SEQ ID No 1 from nucleotide 234 to nucleotide 255
the nucleotide sequence of SEQ ID No 1 from nucleotide 294 to nucleotide 215
the nucleotide sequence of SEQ ID No 1 from nucleotide 247 to nucleotide 266—the nucleotide sequence of SEQ ID No 1 from nucleotide 248 to nucleotide 266 the nucleotide sequence of SEQ ID No 1 from nucleotide 249 to nucleotide 266 b. foreign DNA sequence recognizing primers for use with 5' flanking sequence recognizing primers:

the complement of the nucleotide sequence of SEQ ID No 1 from nucleotide 781 to nucleotide 800
the complement of the nucleotide sequence of SEQ ID No 1 from nucleotide 301 to nucleotide 320
the complement of the nucleotide sequence of SEQ ID No 1 from nucleotide 303 to nucleotide 322
the complement of the nucleotide sequence of SEQ ID No 1 from nucleotide 442 to nucleotide 461—the complement of the nucleotide sequence of SEQ ID No 1 from nucleotide 444 to nucleotide 463
the complement of the nucleotide sequence of SEQ ID No 1 from nucleotide 778 to nucleotide 797
the complement of the nucleotide sequence of SEQ ID No 1 from nucleotide 781 to nucleotide 79^
the complement of the nucleotide sequence of SEQ ID No 1 from nucleotide 788 to nucleotide 807
the complement of the nucleotide sequence of SEQ ID No 1 from nucleotide 318 to nucleotide 337
the complement of the nucleotide sequence of SEQ ID No 1 from nucleotide 322 to nucleotide 341
the complement of the nucleotide sequence of SEQ ID No 1 from nucleotide 325 to nucleotide 344
the complement of the nucleotide sequence of SEQ ID No 1 from nucleotide 329 to nucleotide 348
the complement of the nucleotide sequence of SEQ ID No 1 from nucleotide 353 to nucleotide 372
the complement of the nucleotide sequence of SEQ ID No 1 from nucleotide 376 to nucleotide 395
the complement of the nucleotide sequence of SEQ ID No 1 from nucleotide 378 to nucleotide 397
the complement of the nucleotide sequence of SEQ ID No 1 from nucleotide 384 to nucleotide 403
the complement of the nucleotide sequence of SEQ ID No 1 from nucleotide 440 to nucleotide 459
the complement of the nucleotide sequence of SEQ ID No 1 from nucleotide 442 to nucleotide 460
the complement of the nucleotide sequence of SEQ ID No 1 from nucleotide 444 to nucleotide 462
the complement of the nucleotide sequence of SEQ ID No 1 from nucleotide 442 to nucleotide 462 the complement of the nucleotide sequence of SEQ ID No 1 from nucleotide 444 to nucleotide 464
the complement of the nucleotide sequence of SEQ ID No 1 from nucleotide 449 to nucleotide 468
the complement of the nucleotide sequence of SEQ ID No 1 from nucleotide 470
the complement of the nucleotide sequence of SEQ ID No 1 from nucleotide 484 to nucleotide 503
the complement of the nucleotide sequence of SEQ ID No 1 from nucleotide 492 to nucleotide 511
the complement of the nucleotide sequence of SEQ ID No 1 from nucleotide 781 to nucleotide 798
the complement of the nucleotide sequence of SEQ ID No 1 from nucleotide 778 to nucleotide 798
the complement of the nucleotide sequence of SEQ ID No 1 from nucleotide 781 to nucleotide 802
the complement of the nucleotide sequence of SEQ ID No 1 from nucleotide 788 to nucleotide 806
the complement of the nucleotide sequence of SEQ ID No 1 from nucleotide 301 to nucleotide 318
the complement of the nucleotide sequence of SEQ ID No 1 from nucleotide 303 to nucleotide 320
the complement of the nucleotide sequence of SEQ ID No 1 from nucleotide 301 to nucleotide 322
the complement of the nucleotide sequence of SEQ ID No 1 from nucleotide 318 to nucleotide 336
the complement of the nucleotide sequence of SEQ ID No 1 from nucleotide 318 to nucleotide 338
the complement of the nucleotide sequence of SEQ ID No 1 from nucleotide 320 to nucleotide 339
the complement of the nucleotide sequence of SEQ ID No 1 from nucleotide 322 to nucleotide 340 the complement of the nucleotide sequence of SEQ ID No 1 from nucleotide 322 to nucleotide 342
the complement of the nucleotide sequence of SEQ ID No 1 from nucleotide 325 to nucleotide 343
the complement of the nucleotide sequence of SEQ ID No 1 from nucleotide 329 to nucleotide 347
the complement of the nucleotide sequence of SEQ ID No 1 from nucleotide 346 to nucleotide 365
the complement of the nucleotide sequence of SEQ ID No 1 from nucleotide 348 to nucleotide 367
the complement of the nucleotide sequence of SEQ ID No 1 from nucleotide 353 to nucleotide 371
the complement of the nucleotide sequence of SEQ ID No 1 from nucleotide 378 to nucleotide 396
the complement of the nucleotide sequence of SEQ ID No 1 from nucleotide 376 to nucleotide 396
the complement of the nucleotide sequence of SEQ ID No 1 from nucleotide 382 to nucleotide 400
the complement of the nucleotide sequence of SEQ ID No 1 from nucleotide 382 to nucleotide 401
the complement of the nucleotide sequence of SEQ ID No 1 from nucleotide 384 to nucleotide 404
the complement of the nucleotide sequence of SEQ ID No 1 from nucleotide 442 to nucleotide 459
the complement of the nucleotide sequence of SEQ ID No 1 from nucleotide 440 to nucleotide 460
the complement of the nucleotide sequence of SEQ ID No 1 from nucleotide 444 to nucleotide 461
the complement of the nucleotide sequence of SEQ ID No 1 from nucleotide 442 to nucleotide 463
the complement of the nucleotide sequence of SEQ ID No 1 from nucleotide 444 to nucleotide 465—the complement of the nucleotide sequence of SEQ ID No 1 from nucleotide 469 to nucleotide 488
the complement of the nucleotide sequence of SEQ ID No 1 from nucleotide 470 to nucleotide 488
the complement of the nucleotide sequence of SEQ ID No 1 from nucleotide 484 to nucleotide 504 the complement of the nucleotide sequence of SEQ ID No 1 from nucleotide 490 to nucleotide 509
the complement of the nucleotide sequence of SEQ ID No 1 from nucleotide 491 to nucleotide 510
the complement of the nucleotide sequence of SEQ ID No 1 from nucleotide 492 to nucleotide 512
the complement of the nucleotide sequence of SEQ ID No 1 from nucleotide 561 to nucleotide 580
the complement of the nucleotide sequence of SEQ ID No 1 from nucleotide 563 to nucleotide 582
the complement of the nucleotide sequence of SEQ ID No 1 from nucleotide 565 to nucleotide 584
the complement of the nucleotide sequence of SEQ ID No 1 from nucleotide 568 to nucleotide 587
the complement of the nucleotide sequence of SEQ ID No 1 from nucleotide 572 to nucleotide 591
the complement of the nucleotide sequence of SEQ ID No 1 from nucleotide 590 to nucleotide 609
the complement of the nucleotide sequence of SEQ ID No 1 from nucleotide 640 to nucleotide 659
the complement of the nucleotide sequence of SEQ ID No 1 from nucleotide 695 to nucleotide 713
the complement of the nucleotide sequence of SEQ ID No 1 from nucleotide 782 to nucleotide 799
the complement of the nucleotide sequence of SEQ ID No 1 from nucleotide 778 to nucleotide 799—the complement of the nucleotide sequence of SEQ ID No 1 from nucleotide 788 to nucleotide 805
the complement of the nucleotide sequence of SEQ ID No 1 from nucleotide 788 to nucleotide 808
the complement of the nucleotide sequence of SEQ ID No 1 from nucleotide 318 to nucleotide 335
the complement of the nucleotide sequence of SEQ ID No 1 from nucleotide 315 to nucleotide 336
the complement of the nucleotide sequence of SEQ ID No 1 from nucleotide 320 to nucleotide 338
the complement of the nucleotide sequence of SEQ ID No 1 from nucleotide 318 to nucleotide 339
the complement of the nucleotide sequence of SEQ ID No 1 from nucleotide 322 to nucleotide 339
the complement of the nucleotide sequence of SEQ ID No 1 from nucleotide 320 to nucleotide 340
the complement of the nucleotide sequence of SEQ ID No 1 from nucleotide 325 to nucleotide 342
the complement of the nucleotide sequence of SEQ ID No 1 from nucleotide 322 to nucleotide 343
the complement of the nucleotide sequence of SEQ ID No 1 from nucleotide 329 to nucleotide 346
the complement of the nucleotide sequence of SEQ ID No 1 from nucleotide 325 to nucleotide 346
the complement of the nucleotide sequence of SEQ ID No 1 from nucleotide 329 to nucleotide 349
the complement of the nucleotide sequence of SEQ ID No 1 from nucleotide 346 to nucleotide 364
the complement of the nucleotide sequence of SEQ ID No 1 from nucleotide 348 to nucleotide 366
the complement of the nucleotide sequence of SEQ ID No 1 from nucleotide 346 to nucleotide 366—the complement of the nucleotide sequence of SEQ ID No 1 from nucleotide 348 to nucleotide 368
the complement of the nucleotide sequence of SEQ ID No 1 from nucleotide 353 to nucleotide 370
the complement of the nucleotide sequence of SEQ ID No 1 from nucleotide 378 to nucleotide 395
the complement of the nucleotide sequence of SEQ ID No 1 from nucleotide 376 to nucleotide 397
the complement of the nucleotide sequence of SEQ ID No 1 from nucleotide 376 to nucleotide 399
the complement of the nucleotide sequence of SEQ ID No 1 from nucleotide 384 to nucleotide 401
the complement of the nucleotide sequence of SEQ ID No 1 from nucleotide 384 to nucleotide 405
the complement of the nucleotide sequence of SEQ ID No 1 from nucleotide 440 to nucleotide 461
the complement of the nucleotide sequence of SEQ ID No 1 from nucleotide 466 to nucleotide 487
the complement of the nucleotide sequence of SEQ ID No 1 from nucleotide 484 to nucleotide 505
the complement of the nucleotide sequence of SEQ ID No 1 from nucleotide 490 to nucleotide 508
the complement of the nucleotide sequence of SEQ ID No 1 from nucleotide 492 to nucleotide 509
the complement of the nucleotide sequence of SEQ ID No 1 from nucleotide 491 to nucleotide 509
the complement of the nucleotide sequence of SEQ ID No 1 from nucleotide 490 to nucleotide 510
the complement of the nucleotide sequence of SEQ ID No 1 from nucleotide 491 to nucleotide 511
the complement of the nucleotide sequence of SEQ ID No 1 from nucleotide 492 to nucleotide 513 the complement of the nucleotide sequence of SEQ ID No 1 from nucleotide 561 to nucleotide 579
the complement of the nucleotide sequence of SEQ ID No 1 from nucleotide 561 to nucleotide 581
the complement of the nucleotide sequence of SEQ ID No 1 from nucleotide 563 to nucleotide 581
the complement of the nucleotide sequence of SEQ ID No 1 from nucleotide 568 to nucleotide 586
the complement of the nucleotide sequence of SEQ ID No 1 from nucleotide 572 to nucleotide 590
the complement of the nucleotide sequence of SEQ ID No 1 from nucleotide 572 to nucleotide 592
the complement of the nucleotide sequence of SEQ ID No 1 from nucleotide 590 to nucleotide 610
the complement of the nucleotide sequence of SEQ ID No 1 from nucleotide 596 to nucleotide 613
the complement of the nucleotide sequence of SEQ ID No 1 from nucleotide 596 to nucleotide 614
the complement of the nucleotide sequence of SEQ ID No 1 from nucleotide 640 to nucleotide 657
the complement of the nucleotide sequence of SEQ ID No 1 from nucleotide 640 to nucleotide 658
the complement of the nucleotide sequence of SEQ ID No 1 from nucleotide 640 to nucleotide 660
the complement of the nucleotide sequence of SEQ ID No 1 from nucleotide 695 to nucleotide 712
the complement of the nucleotide sequence of SEQ ID No 1 from nucleotide 696 to nucleotide 713
the complement of the nucleotide sequence of SEQ ID No 1 from nucleotide 320 to nucleotide 337
the complement of the nucleotide sequence of SEQ ID No 1 from nucleotide 320 to nucleotide 341 the complement of the nucleotide sequence of SEQ ID No 1 from nucleotide 329 to nucleotide 350
the complement of the nucleotide sequence of SEQ ID No 1 from nucleotide 346 to nucleotide 363
the complement of the nucleotide sequence of SEQ ID No 1 from nucleotide 348 to nucleotide 365
the complement of the nucleotide sequence of SEQ ID No 1 from nucleotide 346 to nucleotide 367
the complement of the nucleotide sequence of SEQ ID No 1 from nucleotide 348 to nucleotide 369 the complement of the nucleotide sequence of SEQ ID No 1 from nucleotide 354 to nucleotide 371
the complement of the nucleotide sequence of SEQ ID No 1 from nucleotide 382 to nucleotide 403
the complement of the nucleotide sequence of SEQ ID No 1 from nucleotide 482 to nucleotide 503
the complement of the nucleotide sequence of SEQ ID No 1 from nucleotide 491 to nucleotide 518
the complement of the nucleotide sequence of SEQ ID No 1 from nucleotide 490 to nucleotide 511
the complement of the nucleotide sequence of SEQ ID No 1 from nucleotide 491 to nucleotide 512
the complement of the nucleotide sequence of SEQ ID No 1 from nucleotide 563 to nucleotide 580
the complement of the nucleotide sequence of SEQ ID No 1 from nucleotide 563 to nucleotide 582
the complement of the nucleotide sequence of SEQ ID No 1 from nucleotide 565 to nucleotide 582
the complement of the nucleotide sequence of SEQ ID No 1 from nucleotide 563 to nucleotide 584
the complement of the nucleotide sequence of SEQ ID No 1 from nucleotide 568 to nucleotide 585—the complement of the nucleotide sequence of SEQ ID No 1 from nucleotide 562 to nucleotide 589
the complement of the nucleotide sequence of SEQ ID No 1 from nucleotide 572 to nucleotide 593
the complement of the nucleotide sequence of SEQ ID No 1 from nucleotide 584 to nucleotide 605
the complement of the nucleotide sequence of SEQ ID No 1 from nucleotide 590 to nucleotide 607
the complement of the nucleotide sequence of SEQ ID No 1 from nucleotide 590 to nucleotide 611
the complement of the nucleotide sequence of SEQ ID No 1 from nucleotide 596 to nucleotide 615
the complement of the nucleotide sequence of SEQ ID No 1 from nucleotide 599 to nucleotide 618
the complement of the nucleotide sequence of SEQ ID No 1 from nucleotide 540 to nucleotide 661
the complement of the nucleotide sequence of SEQ ID No 1 from nucleotide 779 to nucleotide 798
the complement of the nucleotide sequence of SEQ ID No 1 from nucleotide 788 to nucleotide 809
the complement of the nucleotide sequence of SEQ ID No 1 from nucleotide 568 to nucleotide 589
the complement of the nucleotide sequence of SEQ ID No 1 from nucleotide 596 to nucleotide 616
the complement of the nucleotide sequence of SEQ ID No 1 from nucleotide 599 to nucleotide 619
the complement of the nucleotide sequence of SEQ ID No 1 from nucleotide 745 to nucleotide 762
the complement of the nucleotide sequence of SEQ ID No 1 from nucleotide 779 to nucleotide 797
the complement of the nucleotide sequence of SEQ ID No 1 from nucleotide 779 to nucleotide 799—the complement of the nucleotide sequence of SEQ ID No 1 from nucleotide 786 to nucleotide 805
the complement of the nucleotide sequence of SEQ ID No 1 from nucleotide 596 to nucleotide 617
the complement of the nucleotide sequence of SEQ ID No 1 from nucleotide 599 to nucleotide 620
the complement of the nucleotide sequence of SEQ ID No 1 from nucleotide 779 to nucleotide 796
the complement of the nucleotide sequence of SEQ ID No 1 from nucleotide 779 to nucleotide 800
the complement of the nucleotide sequence of SEQ ID No 1 from nucleotide 786 to nucleotide 804
the complement of the nucleotide sequence of SEQ ID No 1 from nucleotide 314 to nucleotide 335
the complement of the nucleotide sequence of SEQ ID No 1 from nucleotide 786 to nucleotide 803
the complement of the nucleotide sequence of SEQ ID No 1 from nucleotide 786 to nucleotide 806
the complement of the nucleotide sequence of SEQ ID No 1 from nucleotide 296 to nucleotide 315 c. foreign DNA sequence recognizing primers for use with 3' flanking sequence recognizing primers:

the complement of the nucleotide sequence of SEQ ID No 2 from nucleotide 1413 to nucleotide 1432
the complement of the nucleotide sequence of SEQ ID No 2 from nucleotide 721 to nucleotide 740
the complement of the nucleotide sequence of SEQ ID No 2 from nucleotide 767 to nucleotide 786
the complement of the nucleotide sequence of SEQ ID No 2 from nucleotide 1185 to nucleotide 1204—the complement of the nucleotide sequence of SEQ ID No 2 from nucleotide 1332 to nucleotide 1351
the complement of the nucleotide sequence of SEQ ID No 2 from nucleotide 1413 to nucleotide 1431
the complement of the nucleotide sequence of SEQ ID No 2 from nucleotide 1413 to nucleotide 1433
the complement of the nucleotide sequence of SEQ ID No 2 from nucleotide 503 to nucleotide 522
the complement of the nucleotide sequence of SEQ ID No 2 from nucleotide 507 to nucleotide 526
the complement of the nucleotide sequence of SEQ ID No 2 from nucleotide 721 to nucleotide 739
the complement of the nucleotide sequence of SEQ ID No 2 from nucleotide 722 to nucleotide 741
the complement of the nucleotide sequence of SEQ ID No 2 from nucleotide 721 to nucleotide 741
the complement of the nucleotide sequence of SEQ ID No 2 from nucleotide 770 to nucleotide 789
the complement of the nucleotide sequence of SEQ ID No 2 from nucleotide 775 to nucleotide 794
the complement of the nucleotide sequence of SEQ ID No 2 from nucleotide 1135 to nucleotide 1154
the complement of the nucleotide sequence of SEQ ID No 2 from nucleotide 1185 to nucleotide 1202
the complement of the nucleotide sequence of SEQ ID No 2 from nucleotide 1185 to nucleotide 1205
the complement of the nucleotide sequence of SEQ ID No 2 from nucleotide 1191 to nucleotide 1210
the complement of the nucleotide sequence of SEQ ID No 2 from nucleotide 1332 to nucleotide 1350
the complement of the nucleotide sequence of SEQ ID No 2 from nucleotide 1332 to nucleotide 1352—the complement of the nucleotide sequence of SEQ ID No 2 from nucleotide 1413 to nucleotide 1430
the complement of the nucleotide sequence of SEQ ID No 2 from nucleotide 506 to nucleotide 525
the complement of the nucleotide sequence of SEQ ID No 2 from nucleotide 507 to nucleotide 525
the complement of the nucleotide sequence of SEQ ID No 2 from nucleotide 507 to nucleotide 527
the complement of the nucleotide sequence of SEQ ID No 2 from nucleotide 721 to nucleotide 738
the complement of the nucleotide sequence of SEQ ID No 2 from nucleotide 722 to nucleotide 740
the complement of the nucleotide sequence of SEQ ID No 2 from nucleotide 721 to nucleotide 742
the complement of the nucleotide sequence of SEQ ID No 2 from nucleotide 775 to nucleotide 793 the complement of the nucleotide sequence of SEQ ID No 2 from nucleotide 775 to nucleotide 795
the complement of the nucleotide sequence of SEQ ID No 2 from nucleotide 135 to nucleotide 1153
the complement of the nucleotide sequence of SEQ ID No 2 from nucleotide 1135 to nucleotide 1155
the complement of the nucleotide sequence of SEQ ID No 2 from nucleotide 1185 to nucleotide 1206
the complement of the nucleotide sequence of SEQ ID No 2 from nucleotide 1191 to nucleotide 1209
the complement of the nucleotide sequence of SEQ ID No 2 from nucleotide 1316 to nucleotide 1335
the complement of the nucleotide sequence of SEQ ID No 2 from nucleotide 1325 to nucleotide 1344 the complement of the nucleotide sequence of SEQ ID No 2 from nucleotide 1332 to nucleotide 1353
the complement of the nucleotide sequence of SEQ ID No 2 from nucleotide 1413 to nucleotide 1434
the complement of the nucleotide sequence of SEQ ID No 2 from nucleotide 507 to nucleotide 528
the complement of the nucleotide sequence of SEQ ID No 2 from nucleotide 722 to nucleotide 739
the complement of the nucleotide sequence of SEQ ID No 2 from nucleotide 725 to nucleotide 742
the complement of the nucleotide sequence of SEQ ID No 2 from nucleotide 730 to nucleotide 749
the complement of the nucleotide sequence of SEQ ID No 2 from nucleotide 770 to nucleotide 787
the complement of the nucleotide sequence of SEQ ID No 2 from nucleotide 770 to nucleotide 791
the complement of the nucleotide sequence of SEQ ID No 2 from nucleotide 771 to nucleotide 792
the complement of the nucleotide sequence of SEQ ID No 2 from nucleotide 775 to nucleotide 792
the complement of the nucleotide sequence of SEQ ID No 2 from nucleotide 775 to nucleotide 796
the complement of the nucleotide sequence of SEQ ID No 2 from nucleotide 1153 to nucleotide 1134
the complement of the nucleotide sequence of SEQ ID No 2 from nucleotide 1135 to nucleotide 1156 the complement of the nucleotide sequence of SEQ ID No 2 from nucleotide 1187 to nucleotide 1206
the complement of the nucleotide sequence of SEQ ID No 2 from nucleotide 1191 to nucleotide 1208
the complement of the nucleotide sequence of SEQ ID No 2 from nucleotide 1191 to nucleotide 1212 the complement of the nucleotide sequence of SEQ ID No 2 from nucleotide 1325 to nucleotide 1343
the complement of the nucleotide sequence of SEQ ID No 2 from nucleotide 1325 to nucleotide 1345
the complement of the nucleotide sequence of SEQ ID No 2 from nucleotide 1367 to nucleotide 1384
the complement of the nucleotide sequence of SEQ ID No 2 from nucleotide 1511 to nucleotide 1528
the complement of the nucleotide sequence of SEQ ID No 2 from nucleotide 506 to nucleotide 527
the complement of the nucleotide sequence of SEQ ID No 2 from nucleotide 730 to nucleotide 750
the complement of the nucleotide sequence of SEQ ID No 2 from nucleotide 1187 to nucleotide 1204
the complement of the nucleotide sequence of SEQ ID No 2 from nucleotide 1187 to nucleotide 1205
the complement of the nucleotide sequence of SEQ ID No 2 from nucleotide 1249 to nucleotide 1266
the complement of the nucleotide sequence of SEQ ID No 2 from nucleotide 1325 to nucleotide 1342
the complement of the nucleotide sequence of SEQ ID No 2 from nucleotide 1325 to nucleotide 1346
the complement of the nucleotide sequence of SEQ ID No 2 from nucleotide 730 to nucleotide 751
the complement of the nucleotide sequence of SEQ ID No 2 from nucleotide 1187 to nucleotide 1208
the complement of the nucleotide sequence of SEQ ID No 2 from nucleotide 1334 to nucleotide 1353
the complement of the nucleotide sequence of SEQ ID No 2 from nucleotide 1334 to nucleotide 1352
the complement of the nucleotide sequence of SEQ ID No 2 from nucleotide 1334 to nucleotide 1354—the complement of the nucleotide sequence of SEQ ID No 2 from nucleotide 1334 to nucleotide 1351
the complement of the nucleotide sequence of SEQ ID No 2 from nucleotide 1334 to nucleotide 1355
the complement of the nucleotide sequence of SEQ ID No 2 from nucleotide 754 to nucleotide 771
the complement of the nucleotide sequence of SEQ ID No 2 from nucleotide 842 to nucleotide 863
the complement of the nucleotide sequence of SEQ ID No 2 from nucleotide 732 to nucleotide 751
the complement of the nucleotide sequence of SEQ ID No 2 from nucleotide 732 to nucleotide 750
flanking sequence recognizing primers:
the nucleotide sequence of SEQ ID No 2 from nucleotide 284 to nucleotide 303
the nucleotide sequence of SEQ ID No 2 from nucleotide 285 to nucleotide 305
the nucleotide sequence of SEQ ID No 2 from nucleotide 289 to nucleotide 308
the nucleotide sequence of SEQ ID No 2 from nucleotide 160 to nucleotide 179
the nucleotide sequence of SEQ ID No 2 from nucleotide 162 to nucleotide 181—the nucleotide sequence of SEQ ID No 2 from nucleotide 283 to nucleotide 303
the nucleotide sequence of SEQ ID No 2 from nucleotide 284 to nucleotide 304 the nucleotide sequence of SEQ ID No 2 from nucleotide 286 to nucleotide 304
the nucleotide sequence of SEQ ID No 2 from nucleotide 287 to nucleotide 306 the nucleotide sequence of SEQ ID No 2 from nucleotide 288 to nucleotide 308—the nucleotide sequence of SEQ ID No 2 from nucleotide 290 to nucleotide 308 the nucleotide sequence of SEQ ID No 2 from nucleotide 394 to nucleotide 413
the nucleotide sequence of SEQ ID No 2 from nucleotide 398 to nucleotide 417
the nucleotide sequence of SEQ ID No 2 from nucleotide 399 to nucleotide 418
the nucleotide sequence of SEQ ID No 2 from nucleotide 400 to nucleotide 418—the nucleotide sequence of SEQ ID No 2 from nucleotide 119 to nucleotide 138 the nucleotide sequence of SEQ ID No 2 from nucleotide 161 to nucleotide 179
the nucleotide sequence of SEQ ID No 2 from nucleotide 161 to nucleotide 181—the nucleotide sequence of SEQ ID No 2 from nucleotide 184 to nucleotide 203
the nucleotide sequence of SEQ ID No 2 from nucleotide 192 to nucleotide 211 the nucleotide sequence of SEQ ID No 2 from nucleotide 193 to nucleotide 212
the nucleotide sequence of SEQ ID No 2 from nucleotide 195 to nucleotide 214—the nucleotide sequence of SEQ ID No 2 from nucleotide 241 to nucleotide 260 the nucleotide sequence of SEQ ID No 2 from nucleotide 283 to nucleotide 304 the nucleotide sequence of SEQ ID No 2 from nucleotide 286 to nucleotide 303 the nucleotide sequence of SEQ ID No 2 from nucleotide 286 to nucleotide 306 the nucleotide sequence of SEQ ID No 2 from nucleotide 287 to nucleotide 304—the nucleotide sequence of SEQ ID No 2 from nucleotide 287 to nucleotide 308
the nucleotide sequence of SEQ ID No 2 from nucleotide 288 to nucleotide 306
the nucleotide sequence of SEQ ID No 2 from nucleotide 366 to nucleotide 385
the nucleotide sequence of SEQ ID No 2 from nucleotide 393 to nucleotide 412
the nucleotide sequence of SEQ ID No 2 from nucleotide 395 to nucleotide 413—the nucleotide sequence of SEQ ID No 2 from nucleotide 398 to nucleotide 418
the nucleotide sequence of SEQ ID No 2 from nucleotide 399 to nucleotide 417
the nucleotide sequence of SEQ ID No 2 from nucleotide 400 to nucleotide 417
the nucleotide sequence of SEQ ID No 2 from nucleotide 401 to nucleotide 418 the nucleotide sequence of SEQ ID No 2 from nucleotide 430 to nucleotide 449—the nucleotide sequence of SEQ ID No 2 from nucleotide 81 to nucleotide 100
the nucleotide sequence of SEQ ID No 2 from nucleotide 90 to nucleotide 109
the nucleotide sequence of SEQ ID No 2 from nucleotide 159 to nucleotide 179
the nucleotide sequence of SEQ ID No 2 from nucleotide 160 to nucleotide 181 the nucleotide sequence of SEQ ID No 2 from nucleotide 185 to nucleotide 203—the nucleotide sequence of SEQ ID No 2 from nucleotide 191 to nucleotide 211
the nucleotide sequence of SEQ ID No 2 from nucleotide 192 to nucleotide 212
the nucleotide sequence of SEQ ID No 2 from nucleotide 193 to nucleotide 211
the nucleotide sequence of SEQ ID No 2 from nucleotide 194 to nucleotide 212
the nucleotide sequence of SEQ ID No 2 from nucleotide 194 to nucleotide 214—the nucleotide sequence of SEQ ID No 2 from nucleotide 196 to nucleotide 215 the nucleotide sequence of SEQ ID No 2 from nucleotide 196 to nucleotide 214
the nucleotide sequence of SEQ ID No 2 from nucleotide 219 to nucleotide 238—the nucleotide sequence of SEQ ID No 2 from nucleotide 240 to nucleotide 260
the nucleotide sequence of SEQ ID No 2 from nucleotide 242 to nucleotide 261 the nucleotide sequence of SEQ ID No 2 from nucleotide 242 to nucleotide 260
the nucleotide sequence of SEQ ID No 2 from nucleotide 275 to nucleotide 294—the nucleotide sequence of SEQ ID No 2 from nucleotide 285 to nucleotide 306
the nucleotide sequence of SEQ ID No 2 from nucleotide 289 to nucleotide 306
the nucleotide sequence of SEQ ID No 2 from nucleotide 315 to nucleotide 334
the nucleotide sequence of SEQ ID No 2 from nucleotide 319 to nucleotide 338
the nucleotide sequence of SEQ ID No 2 from nucleotide 366 to nucleotide 383—the nucleotide sequence of SEQ ID No 2 from nucleotide 372 to nucleotide 391
the nucleotide sequence of SEQ ID No 2 from nucleotide 392 to nucleotide 412
the nucleotide sequence of SEQ ID No 2 from nucleotide 392 to nucleotide 413
the nucleotide sequence of SEQ ID No 2 from nucleotide 394 to nucleotide 412
the nucleotide sequence of SEQ ID No 2 from nucleotide 397 to nucleotide 417—the nucleotide sequence of SEQ ID No 2 from nucleotide 397 to nucleotide 418
the nucleotide sequence of SEQ ID No 2 from nucleotide 424 to nucleotide 443
the nucleotide sequence of SEQ ID No 2 from nucleotide 429 to nucleotide 449
the nucleotide sequence of SEQ ID No 2 from nucleotide 431 to nucleotide 450
the nucleotide sequence of SEQ ID No 2 from nucleotide 431 to nucleotide 449—the nucleotide sequence of SEQ ID No 2 from nucleotide 439 to nucleotide 458
the nucleotide sequence of SEQ ID No 2 from nucleotide 447 to nucleotide 466
the nucleotide sequence of SEQ ID No 2 from nucleotide 481 to nucleotide 500
the nucleotide sequence of SEQ ID No 2 from nucleotide 507 to nucleotide 526
the nucleotide sequence of SEQ ID No 2 from nucleotide 79 to nucleotide 96—the nucleotide sequence of SEQ ID No 2 from nucleotide 80 to nucleotide 100
the nucleotide sequence of SEQ ID No 2 from nucleotide 82 to nucleotide 100 the nucleotide sequence of SEQ ID No 2 from nucleotide 89 to nucleotide 109 the nucleotide sequence of SEQ ID No 2 from nucleotide 91 to nucleotide 109 the nucleotide sequence of SEQ ID No 2 from nucleotide 121 to nucleotide 138—the nucleotide sequence of SEQ ID No 2 from nucleotide 184 to nucleotide 202 the nucleotide sequence of SEQ ID No 2 from nucleotide 186 to nucleotide 203
the nucleotide sequence of SEQ ID No 2 from nucleotide 190 to nucleotide 211—the nucleotide sequence of SEQ ID No 2 from nucleotide 191 to nucleotide 212
the nucleotide sequence of SEQ ID No 2 from nucleotide 193 to nucleotide 214 the nucleotide sequence of SEQ ID No 2 from nucleotide 194 to nucleotide 211
the nucleotide sequence of SEQ ID No 2 from nucleotide 195 to nucleotide 215—the nucleotide sequence of SEQ ID No 2 from nucleotide 195 to nucleotide 212
the nucleotide sequence of SEQ ID No 2 from nucleotide 218 to nucleotide 238
the nucleotide sequence of SEQ ID No 2 from nucleotide 220 to nucleotide 238
the nucleotide sequence of SEQ ID No 2 from nucleotide 221 to nucleotide 238
the nucleotide sequence of SEQ ID No 2 from nucleotide 239 to nucleotide 260—the nucleotide sequence of SEQ ID No 2 from nucleotide 241 to nucleotide 261
the nucleotide sequence of SEQ ID No 2 from nucleotide 277 to nucleotide 294
the nucleotide sequence of SEQ ID No 2 from nucleotide 282 to nucleotide 303 the nucleotide sequence of SEQ ID No 2 from nucleotide 314 to nucleotide 334 the nucleotide sequence of SEQ ID No 2 from nucleotide 316 to nucleotide 334—the nucleotide sequence of SEQ ID No 2 from nucleotide 318 to nucleotide 338
the nucleotide sequence of SEQ ID No 2 from nucleotide 320 to nucleotide 338 the nucleotide sequence of SEQ ID No 2 from nucleotide 371 to nucleotide 391 the nucleotide sequence of SEQ ID No 2 from nucleotide 391 to nucleotide 412
the nucleotide sequence of SEQ ID No 2 from nucleotide 395 to nucleotide 412—the nucleotide sequence of SEQ ID No 2 from nucleotide 396 to nucleotide 417
the nucleotide sequence of SEQ ID No 2 from nucleotide 423 to nucleotide 443 the nucleotide sequence of SEQ ID No 2 from nucleotide 430 to nucleotide 450 the nucleotide sequence of SEQ ID No 2 from nucleotide 432 to nucleotide 449 the nucleotide sequence of SEQ ID No 2 from nucleotide 438 to nucleotide 458—the nucleotide sequence of SEQ ID No 2 from nucleotide 446 to nucleotide 466
the nucleotide sequence of SEQ ID No 2 from nucleotide 448 to nucleotide 466
the nucleotide sequence of SEQ ID No 2 from nucleotide 449 to nucleotide 466
the nucleotide sequence of SEQ ID No 2 from nucleotide 481 to nucleotide 498
the nucleotide sequence of SEQ ID No 2 from nucleotide 481 to nucleotide 499—the nucleotide sequence of SEQ ID No 2 from nucleotide 482 to nucleotide 500
the nucleotide sequence of SEQ ID No 2 from nucleotide 508 to nucleotide 526
the nucleotide sequence of SEQ ID No 2 from nucleotide 79 to nucleotide 100—the nucleotide sequence of SEQ ID No 2 from nucleotide 83 to nucleotide 100
the nucleotide sequence of SEQ ID No 2 from nucleotide 88 to nucleotide 109
the nucleotide sequence of SEQ ID No 2 from nucleotide 92 to nucleotide 109
the nucleotide sequence of SEQ ID No 2 from nucleotide 185 to nucleotide 202—the nucleotide sequence of SEQ ID No 2 from nucleotide 194 to nucleotide 215
the nucleotide sequence of SEQ ID No 2 from nucleotide 217 to nucleotide 238
the nucleotide sequence of SEQ ID No 2 from nucleotide 240 to nucleotide 261 the nucleotide sequence of SEQ ID No 2 from nucleotide 241 to nucleotide 262 the nucleotide sequence of SEQ ID No 2 from nucleotide 313 to nucleotide 334—the nucleotide sequence of SEQ ID No 2 from nucleotide 317 to nucleotide 338
the nucleotide sequence of SEQ ID No 2 from nucleotide 321 to nucleotide 338
the nucleotide sequence of SEQ ID No 2 from nucleotide 370 to nucleotide 391
the nucleotide sequence of SEQ ID No 2 from nucleotide 422 to nucleotide 443
the nucleotide sequence of SEQ ID No 2 from nucleotide 428 to nucleotide 449—the nucleotide sequence of SEQ ID No 2 from nucleotide 429 to nucleotide 450
the nucleotide sequence of SEQ ID No 2 from nucleotide 437 to nucleotide 458 the nucleotide sequence of SEQ ID No 2 from nucleotide 441 to nucleotide 458 the nucleotide sequence of SEQ ID No 2 from nucleotide 445 to nucleotide 466
the nucleotide sequence of SEQ ID No 2 from nucleotide 482 to nucleotide 499—the nucleotide sequence of SEQ ID No 2 from nucleotide 504 to nucleotide 523
the nucleotide sequence of SEQ ID No 2 from nucleotide 266 to nucleotide 287
the nucleotide sequence of SEQ ID No 2 from nucleotide 446 to nucleotide 465
the nucleotide sequence of SEQ ID No 2 from nucleotide 156 to nucleotide 175
the nucleotide sequence of SEQ ID No 2 from nucleotide 448 to nucleotide 465—the nucleotide sequence of SEQ ID No 2 from nucleotide 155 to nucleotide 175
the nucleotide sequence of SEQ ID No 2 from nucleotide 157 to nucleotide 175
the nucleotide sequence of SEQ ID No 2 from nucleotide 154 to nucleotide 175
the nucleotide sequence of SEQ ID No 2 from nucleotide 312 to nucleotide 329
the nucleotide sequence of SEQ ID No 2 from nucleotide 191 to nucleotide 210—the nucleotide sequence of SEQ ID No 2 from nucleotide 190 to nucleotide 210
the nucleotide sequence of SEQ ID No 2 from nucleotide 192 to nucleotide 210
the nucleotide sequence of SEQ ID No 2 from nucleotide 157 to nucleotide 176—the nucleotide sequence of SEQ ID No 2 from nucleotide 189 to nucleotide 210
the nucleotide sequence of SEQ ID No 2 from nucleotide 193 to nucleotide 210 the nucleotide sequence of SEQ ID No 2 from nucleotide 156 to nucleotide 176 the nucleotide sequence of SEQ ID No 2 from nucleotide 155 to nucleotide 176

As used herein, "the nucleotide sequence of SEQ ID No. Z from position X to position Y" indicates the nucleotide sequence including both nucleotide endpoints.

Preferably, the integration fragment has a length of between 50 and 500 nucleotides, most preferably of between 100 and 350 nucleotides. The specific primers may have a sequence which is between 80 and 100% identical to a sequence within the 5' or 3' flanking region of the elite event and the foreign DNA of the elite event, respectively, provided the mismatches still allow specific identification of the elite event with these primers under optimized PCR conditions. The range of allowable mismatches however, can easily be determined experimentally and are known to a person skilled in the art.

The following table exemplifies the sizes of expected DNA amplicons (or integration fragments) with selected pairs of PCR primers.

| Primer 1 | From position | Primer 2 | To position | Length amplicon |
|---|---|---|---|---|
| HCA150 | 8 | KVM173 | 365 | |
| HCA150 | 8 | YTP228 | 402 | |
| HCA150 | 8 | YTP220 | 594 | |
| HCA150 | 8 | DPA024 | 736 | |
| HCA150 | 8 | YTP245 | 796 | |
| DPA013 | 66 | KVM173 | 365 | |
| DPA013 | 66 | YTP228 | 402 | |
| DPA013 | 66 | YTP220 | 594 | |
| DPA013 | 66 | DPA024 | 736 | |
| DPA013 | 66 | YTP245 | 796 | |
| DPA228 | 292 | KVM173 | 365 | |
| DPA228 | 292 | YTP228 | 402 | 110 |
| DPA228 | 292 | YTP220 | 594 | 302 |
| DPA228 | 292 | DPA024 | 736 | 444 |
| DPA228 | 292 | YTP245 | 796 | 504 |
| YTP170 | 82 | MDB687 | 527 | 445 |
| YTP170 | 82 | SMO022 | 724 | 642 |
| YTP170 | 82 | SMO024 | 1215 | 1133 |
| YTP227 | 237 | MDB687 | 527 | 290 |
| YTP227 | 237 | SMO022 | 724 | 487 |
| YTP227 | 237 | SMO024 | 1215 | 978 |
| MDB688 | 377 | MDB687 | 527 | 150 |
| MDB688 | 377 | SMO022 | 724 | 347 |
| MDB688 | 377 | SMO024 | 1215 | 838 |
| KVM175 | 476 | MDB687 | 527 | 51 |
| KVM175 | 476 | SMO022 | 724 | 248 |
| KVM175 | 476 | SMO024 | 1215 | 739 |

Detection of integration fragments can occur in various ways e.g. via size estimation after gel analysis. The integration fragments may also be directly sequenced. Other sequence specific methods for detection of amplified DNA fragments are also known in the art.

As the sequence of the primers and their relative location in the genome are unique for the elite event, amplification of the integration fragment will occur only in biological samples comprising (the nucleic acid of) the elite event. Preferably when performing a PCR to identify the presence of A5547-127 in unknown samples, a control is included of a set of primers with which a fragment within a "housekeeping gene" of the plant species of the event can be amplified. Housekeeping genes are genes that are expressed in most cell types and which are concerned with basic metabolic activities common to all cells. Preferably, the fragment amplified from the housekeeping gene is a fragment which is larger than the amplified integration fragment. Depending on the samples to be analyzed, other controls can be included.

Standard PCR protocols are described in the art, such as in 'PCR Applications Manual" (Roche Molecular Biochemicals, 2nd Edition, 1999). The optimal conditions for the PCR, including the sequence of the specific primers, is specified in a "PCR identification protocol" for each elite event. It is however understood that a number of parameters in the PCR identification protocol may need to be adjusted to specific laboratory conditions, and may be modified slightly to obtain similar results. For instance, use of a different method for preparation of DNA may require adjustment of, for instance, the amount of primers, polymerase and annealing conditions used. Similarly, the selection of other primers may dictate other optimal conditions for the PCR identification protocol. These adjustments will however be apparent to a person skilled in the art, and are furthermore detailed in current PCR application manuals such as the one cited above.

Alternatively, specific primers can be used to amplify an integration fragment that can be used as a "specific probe" for identifying A5547-127 in biological samples. Contacting nucleic acid of a biological sample, with the probe, under conditions which allow hybridization of the probe with its corresponding fragment in the nucleic acid, results in the formation of a nucleic acid/probe hybrid. The formation of this hybrid can be detected (e.g. labeling of the nucleic acid or probe), whereby the formation of this hybrid indicates the presence of A5547-127. Such identification methods based on hybridization with a specific probe (either on a solid phase carrier or in solution) have been described in the art. The specific probe is preferably a sequence which, under optimized conditions, hybridizes specifically to a region within the 5' or 3' flanking region of the elite event and preferably also comprising part of the foreign DNA contiguous therewith (hereinafter referred to as "specific region"). Preferably, the specific probe comprises a sequence of between 50 and 500 bp, preferably of 100 to 350 bp which is at least 80%, preferably between 80 and 85%, more preferably between 85 and 90%, especially preferably between 90 and 95%, most preferably between 95% and 100% identical (or complementary) to the nucleotide sequence of a specific region. Preferably, the specific probe will comprise a sequence of about 15 to about 100 contiguous nucleotides identical (or complementary) to a specific region of the elite event.

A "kit" as used herein refers to a set of reagents for the purpose of performing the method of the invention, more particularly, the identification of the elite event A5547-127 in biological samples. More particularly, a preferred embodiment of the kit of the invention comprises at least one or two specific primers, as described above. Optionally, the kit can further comprise any other reagent described herein in the PCR identification protocol. Alternatively, according to another embodiment of this invention, the kit can comprise a specific probe, as described above, which specifically hybridizes with nucleic acid of biological samples to identify the presence of A5547-127 therein. Optionally, the kit can further comprise any other reagent (such as but not limited to hybridizing buffer, label) for identification of A5547-127 in biological samples, using the specific probe.

The kit of the invention can be used, and its components can be specifically adjusted, for purposes of quality control (e.g., purity of seed lots), detection of the elite event in plant material or material comprising or derived from plant material, such as but not limited to food or feed products.

As used herein, "sequence identity" with regard to nucleotide sequences (DNA or RNA), refers to the number of positions with identical nucleotides divided by the number of nucleotides in the shorter of the two sequences. The alignment of the two nucleotide sequences is performed by the Wilbur and Lipmann algorithm (Wilbur and Lipmann, 1983, Proc. Nat. Acad. Sci. USA 80:726) using a window-size of 20 nucleotides, a word length of 4 nucleotides, and a gap penalty of 4. Computer-assisted analysis and interpretation of sequence data, including sequence alignment as described above, can, e.g., be conveniently performed using the programs of the Intelligenetics™ Suite (Intelligenetics Inc., CA) or the sequence analysis software package of the Genetics Computer Group (GCG, University of Wisconsin Biotechnology center).

Sequences are indicated as "essentially similar" when such sequences have a sequence identity of at least about 75%, particularly at least about 80%, more particularly at least about 85%, quite particularly about 90%, especially about 95%, more especially about 100%. It is clear than when RNA sequences are said to be essentially similar or have a certain degree of sequence identity with DNA sequences, thymidine (T) in the DNA sequence is considered equal to uracil (U) in the RNA sequence.

The term "primer" as used herein encompasses any nucleic acid that is capable of priming the synthesis of a nascent nucleic acid in a template-dependent process, such as PCR. Typically, primers are oligonucleotides from 10 to 30 nucleotides, but longer sequences can be employed. Primers may be provided in double-stranded form, though the single-stranded form is preferred. Probes can be used as primers, but are designed to bind to the target DNA or RNA and need not be used in an amplification process.

The term "recognizing" as used herein when referring to specific primers, refers to the fact that the specific primers specifically hybridize to a nucleic acid sequence in the elite event under the conditions set forth in the method (such as the conditions of the PCR identification protocol), whereby the specificity is determined by the presence of positive and negative controls.

The term "hybridizing" as used herein when referring to specific probes, refer to the fact that the probe binds to a specific region in the nucleic acid sequence of the elite event under standard stringency conditions. Standard stringency conditions as used herein refers to the conditions for hybridization described herein or to the conventional hybridizing conditions as described by Sambrook et al., 1989 (Molecular Cloning: A Laboratory Manual, Second Edition, Cold Spring Harbour Laboratory Press, NY) which for instance can comprise the following steps: 1) immobilizing plant genomic DNA fragments on a filter, 2) prehybridizing the filter for 1 to 2 hours at 42° C. in 50% formamide, 5×SSPE, 2×Denhardt's reagent and 0.1% SDS, or for 1 to 2 hours at 68° C. in 6×SSC, 2×Denhardt's reagent and 0.1% SDS, 3) adding the hybridization probe which has been labeled, 4) incubating for 16 to 24 hours, 5) washing the filter for 20 min. at room temperature in 1×SSC, 0.1% SDS, 6) washing the filter three times for 20 min. each at 68° C. in 0.2×SSC, 0.1% SDS, and 7) exposing the filter for 24 to 48 hours to X-ray film at −70° C. with an intensifying screen.

As used in herein, a biological samples is a sample of a plant, plant material or products comprising plant material.

The term "plant" is intended to encompass soybean {Glycine max} plant tissues, at any stage of maturity, as well as any cells, tissues, or organs taken from or derived from any such plant, including without limitation, any seeds, leaves, stems, flowers, roots, single cells, gametes, cell cultures, tissue cultures or protoplasts.

"Plant material", as used herein refers to material which is obtained or derived from a plant. Products comprising plant material relate to food, feed or other products which are produced using plant material or can be contaminated by plant material. It is understood that, in the context of the present invention, such biological samples are tested for the presence of nucleic acids specific for A5547-127, implying the presence of nucleic acids in the samples. Thus the methods referred to herein for identifying elite event A5547-127 in biological samples, relate to the identification in biological samples of nucleic acids which comprise the elite event.

As used herein "comprising" is to be interpreted as specifying the presence of the stated features, integers, steps, reagents or components as referred to, but does not preclude the presence or addition of one or more features, integers, steps or components, or groups thereof. Thus, e.g., a nucleic acid or protein comprising a sequence of nucleotides or amino acids, may comprise more nucleotides or amino acids than the actually cited ones, i.e., be embedded in a larger nucleic acid or protein. A chimeric gene comprising a DNA sequence which is functionally or structurally defined, may comprise additional DNA sequences, etc.

The present invention also relates to the development of an elite event A5547-127 in soybean to the plants comprising this event, the progeny obtained from these plants and to the plant cells, or plant material derived from this event. Plants comprising elite event A5547-127 were obtained through as described in example 1.

Soybean plants or plant material comprising A5547-127 can be identified according to the PCR identification protocol described for A5547-127 in Example 2. Briefly, soybean genomic DNA present in the biological sample is amplified by PCR using a primer which specifically recognizes a sequence within the 5' or 3' flanking sequence of A5547-127 such as the primer with the sequence of SEQ ID NO: 15, and a primer which recognizes a sequence in the foreign DNA. such as the primer with the sequence of SEQ ID NO: 13. DNA primers which amplify part of an endogenous soybean sequence are used as positive control for the PCR amplification. If upon PCR amplification, the material yields a fragment of the expected size, the material contains plant material from a soybean plant harboring elite event A5547-127.

Plants harboring A5547-127 are characterized by their glufosinate tolerance, which in the context of the present invention includes that plants are tolerant to the herbicide Liberty™ Tolerance to Liberty™ can be tested in different ways. The leaf paint method as described herein, is most useful when discrimination between resistant and sensitive plants is required, without killing the sensitive ones. Alternatively, tolerance can be tested by Liberty™ spray application. Spray treatments should be made between the leaf stages V3 and V4 for best results. Tolerant plants are characterized by the fact that spraying of the plants with at least 200 grams active ingredient/hectare (g.a.i./ha), preferably 400 g.a.i./ha, and possibly up to 1600 g.a.i./ha (4× the normal field rate), does not kill the plants. A broadcast application should be applied at a rate of 28-34 oz Liberty™. It is best to apply at a volume of 20 gallons of water per acre using a flat fan type nozzle while being careful not to direct spray applications directly into the whorl of the plants to avoid surfactant burn on the leaves. The herbicide effect should appear within 48 hours and be clearly visible within 5-7 days.

Plants harboring A5547-127 can further be characterized by the presence in their cells of phosphinothricin acetyl transferase as determined by a PAT assay (De Block et al, 1987).

Plants harboring A5547-127 are also characterized by having agronomical characteristics that are comparable to commercially available varieties of soybean in the US, in the absence of weed pressure and use of Liberty™ for weed control. It has been observed that the presence of a foreign DNA in the insertion region of the soybean plant genome described herein, confers particularly interesting phenotypic and molecular characteristics to the plants comprising this event. More specifically, the presence of the foreign DNA in this particular region in the genome of these plants, results in plants which display a stable phenotypic expression of the gene of interest without significantly compromising any aspect of desired agronomic performance of the plants.

The following examples describe the identification of the development of tools for the identification of elite event A5547-127 in biological samples.

Unless otherwise stated, all recombinant DNA techniques are carried out according to standard protocols as described in Sambrook et al. (1989) Molecular Cloning: A Laboratory Manual, Second Edition, Cold Spring Harbour Laboratory Press, NY and in Volumes 1 and 2 of Ausubel et al. (1994) Current Protocols in Molecular Biology, Current Protocols, USA. Standard materials and methods for plant molecular work are described in Plant Molecular Biology Labfax (1993) by R. D. D. Croy published by BIOS Scientific Publications Ltd (UK) and Blackwell Scientific Publications, UK.

In the description and examples, reference is made to the following sequences:
SEQ ID No. 1: nucleotide sequence comprising a 5' flanking region of A5547-127
SEQ ID No. 2: nucleotide sequence comprising a 3' flanking region of A5547-127
SEQ ID No. 3: primer HCA150
SEQ ID No. 4: primer DPA013
SEQ ID No. 5: primer DPA228
SEQ ID No. 6: primer KVM173
SEQ ID No. 7: primer YTP228
SEQ ID No. 8: primer YTP220
SEQ ID No. 9: primer DPA024
SEQ ID No. 10: primer YTP245
SEQ ID No. 11: primer YTPI 70
SEQ ID No. 12: primer YTP227
SEQ ID No. 13: primer MDB688
SEQ ID No. 14: primer KVM 175
SEQ ID No. 15: primer MDB687
SEQ ID No. 16: primer SM0022
SEQ ID No. 17: primer SM0024
SEQ ID No. 18: primer 1 for amplification of control fragment
SEQ ID No. 19: primer 2 for amplification of control fragment

BRIEF DESCRIPTION OF THE DRAWINGS

The following Examples, not intended to limit the invention to specific embodiments described, may be understood in conjunction with the accompanying Figure, incorporated herein by reference, in which.

Figure 1:
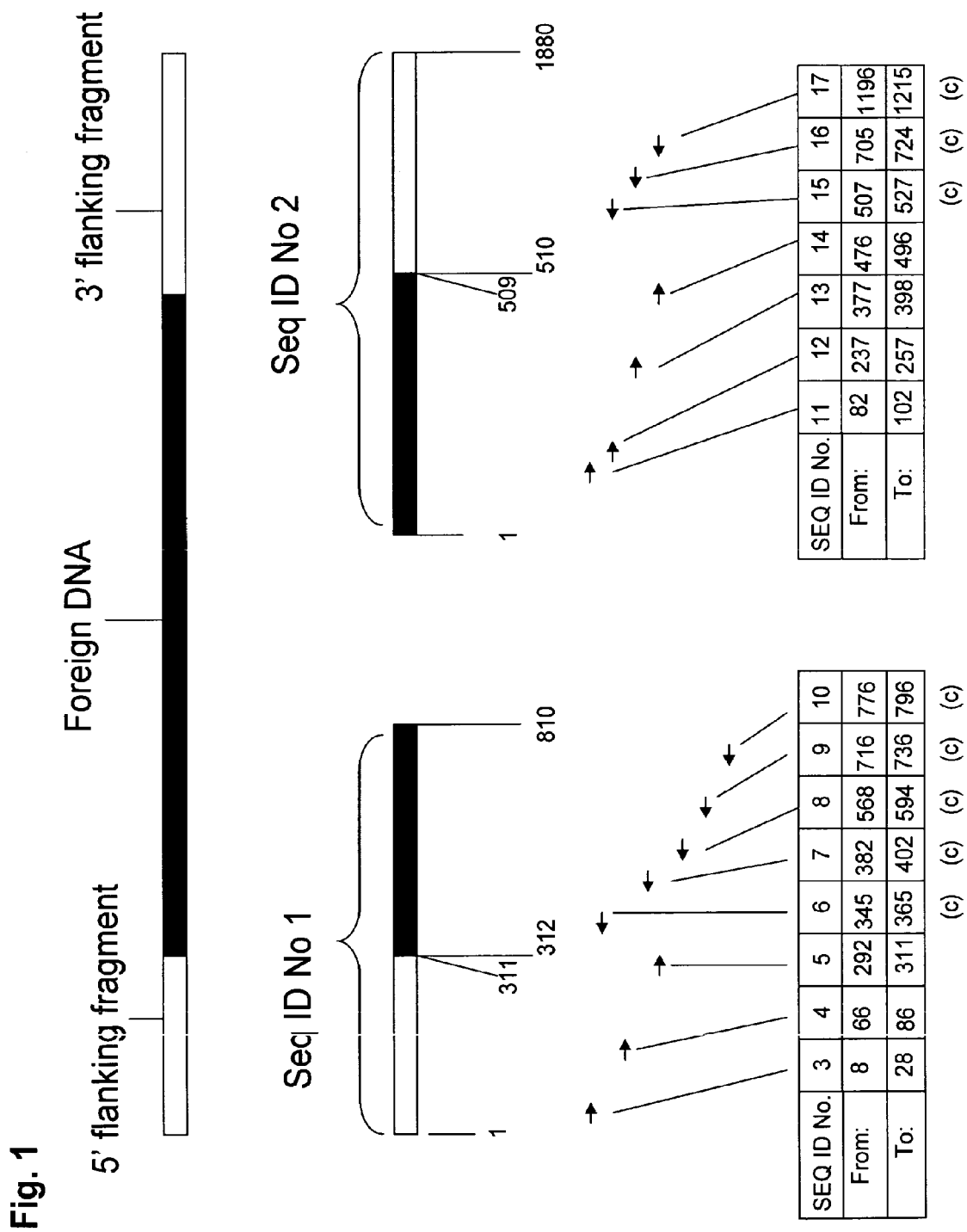
FIG. 1: Schematic representation of the relationship between the cited nucleotide sequences and primers, black bar: foreign DNA; light bar: DNA of plant origin; the figures under the bars represent nucleotide positions; (c) refers to complement of the indicated nucleotide sequence.

lane 2: DNA sample from a transgenic soybean plant not comprising elite event A5547-127; lane 3: control DNA samples from wild-type soybean plants; lane 4: no template control; lane 5: molecular weight marker.

EXAMPLES

1. Identification of the Flanking Regions of Elite Event A5547-127

Herbicide-resistant soybean was developed by transformation of soybean with a vector comprising the coding sequence of a pat gene encoding the enzyme phosphinothricin-acetyl-transferase, under the control of the constitutive 35S promoter from Cauliflower Mosaic virus.

Elite event A5547-127 was selected based on an extensive selection procedure based on good expression and stability of the herbicide resistance gene and its compatibility with optimal agronomic characteristics.

The sequence of the regions flanking the foreign DNA in the A5547-127 event was determined using the thermal asymmetric interlaced (TAIL-) PCR method described by Liu et al. (1995, Plant J. 8(3):457-463). This method utilizes three nested primers in successive reactions together with a shorter arbitrary degenerate primer so that the relative amplification efficiencies of specific and non-specific products can be thermally controlled. The specific primers were selected for annealing to the border of the foreign DNA and based on their annealing conditions. A small amount (5 µl) of unpurified, secondary and tertiary. PCR products were analyzed on a 1% agarose gel. The tertiary PCR product was used for preparative amplification, purified and sequenced on an automated sequencer using the DyeDeoxy Terminator cycle kit.

1.1. Right (5') Flanking Region

The fragment identified as comprising the 5' flanking region obtained by the TAIL-PCR method was completely sequenced (SEQ ID No. 1). The sequence between nucleotide 1 and 311 corresponds to plant DNA, while the sequence between nucleotide 312 and 810 corresponds to foreign DNA.

1.2. Left (3') Flanking Region

The fragment identified as comprising the 3' flanking region obtained by the TAIL-PCR method was completely sequenced (SEQ ID No. 2). The sequence between nucleotide 1 and 509 corresponds to foreign DNA, while the sequence between nucleotide 510 and 1880 corresponds to plant DNA.

2. Development of a Polymerase Chain Reaction Identification Protocol 2.1. Primers Specific primers were developed which recognize sequences within the elite event. More particularly, a primer was developed which recognizes a sequence within the 5' flanking region of A5547-127. A second primer was then selected within the sequence of the foreign DNA so that the primers span a sequence of about 150 nucleotides. The following primers were found to give particularly clear and reproducible results in a
PCR reaction on A5547-127 DNA:

```
                                       (SEQ ID No.: 15)
    MDB687: 5'-TgT.ggT.TAT.ggC.ggT.gCC.ATC-3'
    (target: plant DNA)

(SEQ ID No.: 13)
    MDB688: 5'-TgC.TAC.Agg.CAT.CgT.ggT.gTC-3'
    (tar get: insert DN A i
```

Primers targeting an endogenous sequence are preferably included in the PCR cocktail. These primers serve as an internal control in unknown samples and in the DNA positive control. A positive result with the endogenous primer-pair demonstrates that there is ample DNA of adequate quality in the genomic DNA preparation for a PCR product to be generated. The endogenous primers were selected to recognize a housekeeping gene in *Glycine max*:

```
                                       (SEQ ID No.: 20)
    SOY01: 5'-gTC. AgCCAC. ACA.gTg.CCT.AT-3'
    (located in Glycine max actin 1 gene
    (Accession JO 1298))

(SEQ ID No.: 21)
    SOY02: 5'-gTT.ACC.gTA.CAg.gTC.TTT.CC-3'
    (located in Glycine max actin 1 gene
    (Accession JO 1298))
```

2.2. Amplified Fragments

The expected amplified fragments in the PCR reaction are:
For primer pair SOY01—SOY02: 413 bp (endogenous control) For primer pair MDB688-MDB687: 151 bp (A5547-127 elite Event)

2.3. Template DNA Template DNA was prepared from a leaf punch according to Edwards et al. (Nucleic Acid Research, 19, pi 349, 1991). When using DNA prepared with other methods, a test run utilizing different amounts of template should be done. Usually 50 ng of genomic template DNA yields the best results.

2.4. Assigned Positive and Negative Controls

To avoid false positives or negatives, it was determined that the following positive and negative controls should be included in a PCR run:

Master Mix control (DNA negative control). This is a PCR in which no DNA is added to the reaction. When the expected result, no PCR products, is observed this indicates that the PCR cocktail was not contaminated with target DNA.

A DNA positive control (genomic DNA sample known to contain the transgenic sequences). Successful amplification of this positive control demonstrates that the PCR was run under conditions which allow for the amplification of target sequences.

A wild-type DNA control. This is a PCR in which the template DNA provided is genomic DNA prepared from a non-transgenic plant. When the expected result, no amplification of a transgene PCR product but amplification of the endogenous PCR product, is observed this indicates that there is no detectable transgene background amplification in a genomic DNA sample.

2.5. PCR Conditions

Optimal results were obtained under the following conditions:

| the PCR mix for 25 µl reactions contains: |
| --- |
| 2.5 µl template DNA |
| 2.5 µl 10x Amplification Buffer (supplied with Taq polymerase) |
| 0.5 µl 10 mM dNTP's |
| 0.5 µl MDB688 (lO pmoles/µl) |
| 0.5 µl MDB687 (lO pmoles/µl) |
| 0.25 µi SOYOi (ipmoies/µi) |
| 0.25 µl SOY02 (lO pmoles/µl) |
| 0.1 µl Taq DNA polymerase (5 units/µl) |
| water up to 25 µl | the thermocycling profile to be followed for optimal results is the following:

|  |  |
|---|---|
|  | 4 min. at 95° C. |
| Followed by: | 1 min. at 95° C. |
|  | 1 min. at 57° C. |
|  | 2 min. at 72° C. |
|  | For 5 cycles |
| Followed by: | 30 sec. at 92° C. |
|  | 30 sec. at 57° C. |
|  | 1 min. at 72° C. |
|  | For 25 cycles |
| Followed by: | 5 minutes at 72° C. |

2.6. Agarose gel analysis To optimally visualise the results of the PCR it was determined that between 10 and 20 µl of the PCR samples should be applied on a 1.5% agarose gel (Trisborate buffer) with an appropriate molecular weight marker (e.g. 1OObp ladder PHARMACIA).

2 7 Validation of the Results

It was determined that data from transgenic plant DNA samples within a single PCR run and a single PCR cocktail should not be acceptable unless 1) the DNA positive control shows the expected PCR products (transgenic and endogenous fragments), 2) the DNA negative control is negative for PCR amplification (no fragments) and 3) the wild-type DNA control shows the expected result (endogenous fragment amplification).

When following the PCR Identification Protocol for A5547-127 as described above, lanes showing visible amounts of the transgenic and endogenous PCR products of the expected sizes, indicate that the corresponding plant from which the genomic template DNA was prepared, has inherited the A5547-127 elite event. Lanes not showing visible amounts of either of the transgenic PCR products and showing visible amounts of the endogenous PCR product, indicate that the corresponding plant from which the genomic template DNA was prepared, does not comprise the elite event. Lanes not showing visible amounts of the endogenous and transgenic PCR products, indicate that the quality and/or quantity of the genomic DNA didn't allow for a PCR product to be generated. These plants cannot be scored. The genomic DNA preparation should be repeated and a new PCR run, with the appropriate controls, has to be performed.

2.8. Use of Discriminating PCR Protocol to Identify A5547-127

Before attempting to screen unknowns, a test run, with all appropriate controls, has to be performed. The developed protocol might require optimization for components that may differ between labs (template DNA preparation, Taq DNA polymerase, quality of the primers, dNTP's, thermocyler, etc.).

Amplification of the endogenous sequence plays a key role in the protocol. One has to attain PCR and thermocycling conditions that amplify equimolar quantities of both the endogenous and transgenic sequence in a known transgenic genomic DNA template. Whenever the targeted endogenous fragment is not amplified or whenever the targeted sequences are not amplified with the same ethidium bromide staining intensities, as iiiHσpH Iw aσarnQp σpl plprtrnnhnrpçi*: nntimiVatinn of the PCR conditions may be required.

*Glycine max* leaf material from a number of plants, some of which comprising A5547-127 were tested according to the above-described protocol. Samples from elite event A5547-127 and from *Glycine max* wild-type were taken as positive and negative controls, respectively.

Figure 2:
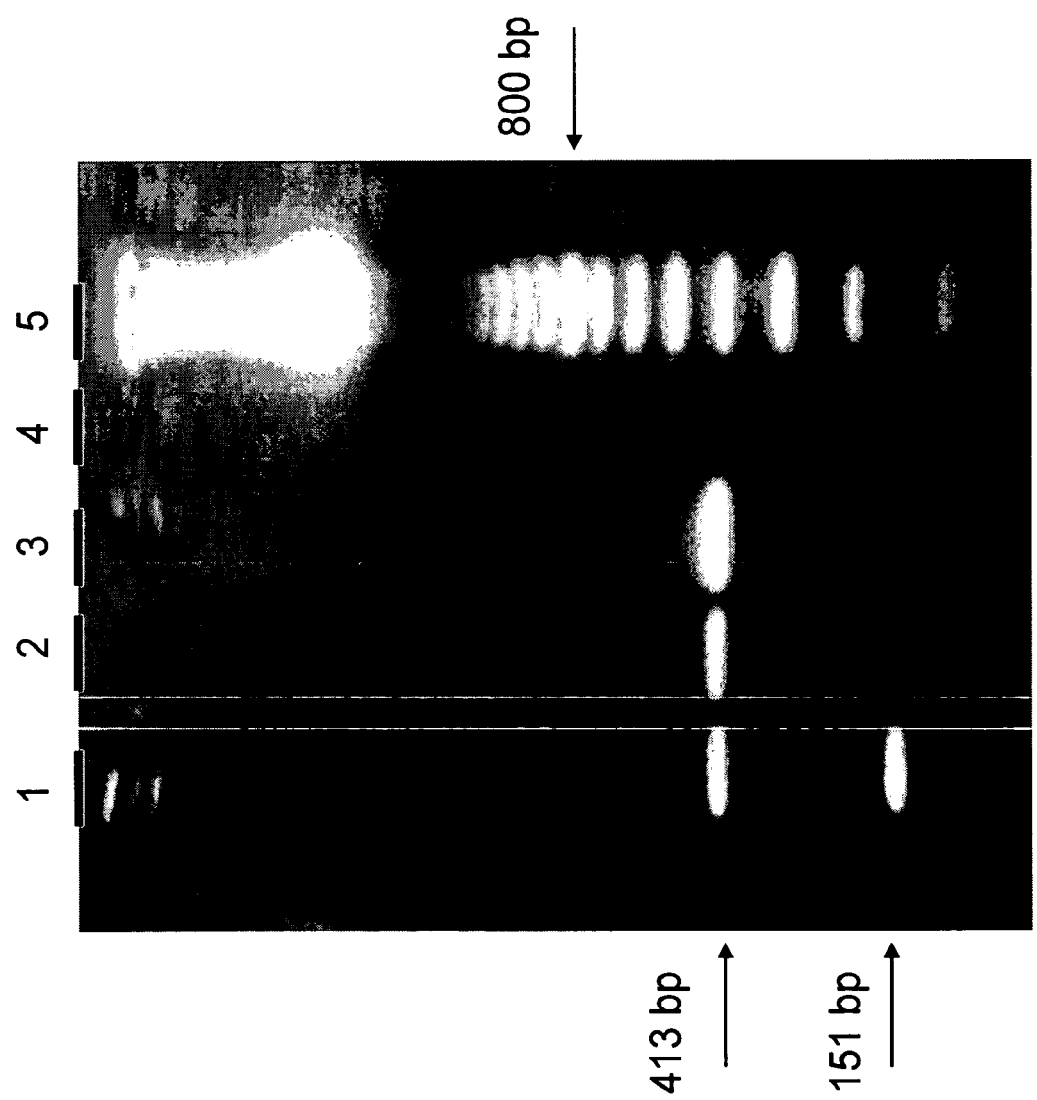
FIG. 2: PCR Identification protocol developed for A5547-127. Loading sequence of the gel: Lane1: DNA sample from soybean plants comprising the transgenic event A5547-127.

FIG. 2 illustrates the result obtained with the elite event PCR identification protocol for A5547-127 on a number of soybean plant samples (lanes 1 to 14). The samples in lane 1 were found to contain the elite event as the 185 bp band is detected, while the samples in lanes 2, 3 and 4 do not comprise A5547-127. Lane 2 comprises another soybean elite event, lane 3 represents a non-transgenic *Glycine max* control; lane 4 represents the negative control (water) sample, and lane 5 represents the Molecular Weight Marker (100 bp).

3. Use of a Specific Integration Fragment as a Probe for Detection of Material Comprising A5547-127

A specific integration fragment of A5547-127 is obtained by PCR amplification using specific primers MDB687 (SEQ ID No. 15) and MDB688 (SEQ ID No. 13) or by chemical synthesis and is labeled. This integration fragment is used as a specific probe for the detection of A5547-127 in biological samples. Nucleic acid is extracted from the samples according to standard procedures. This nucleic acid is then contacted with the specific probe under hybridization conditions which are optimized to allow formation of a hybrid. The formation of the hybrid is then detected to indicate the presence of A5547-127 nucleic acid in the sample. Optionally, the nucleic acid in the samples is amplified using the specific primers prior to contact with the specific probe. Alternatively, the nucleic acid is labeled prior to contact with the specific probe instead of the integration fragment. Optionally, the specific probe is attached to a solid carrier (such as, but not limited to a filter, strip or beads), prior to contact with the samples.

The invention claimed is:

1. A kit comprising a primer pair, one primer of said pair recognizing the 5' flanking region of A5547-127, and the other primer of said pair recognizing the foreign DNA contiguous with said 5' flanking region, or one primer of said pair recognizing the 3' flanking region of A5547-127 and the other primer of said pair recognizing the foreign DNA contiguous with said 3' flanking region, wherein said 5' flanking region comprises the nucleotide sequence of SEQ ID No 1 from nucleotide 1 to nucleotide 311, said 3' flanking region comprising the nucleotide sequence of the complement of SEQ ID No 2 from nucleotide 510 to nucleotide 1880, wherein said foreign DNA contiguous with said 5' flanking region comprises the nucleotide sequence of the complement of SEQ ID No. 1 from nucleotide 312 to nucleotide 810, and wherein said foreign DNA contiguous with said 3' flanking region comprises the nucleotide sequence of SEQ ID No 2 from nucleotide 1 to nucleotide 509.

2. The kit of claim 1, wherein said first primer recognizing the 5' flanking region consists of a nucleotide sequence of 17 to 200 consecutive nucleotides selected from the nucleotide sequence of SEQ ID No 1 from nucleotide 1 to nucleotide 311, and said second primer recognizing a sequence within the foreign DNA consists of 17 to 200 consecutive nucleotides selected from the nucleotide sequence of the complement of SEQ ID No 1 from nucleotide 312 to nucleotide 810, or said first primer recognizing the 3' flanking region of A5547-127 consists of a nucleotide sequence of 17 to 200 consecutive nucleotides selected from the nucleotide sequence of the complement of SEQ ID No 2 from nucleotide 510 to nucleotide 1880, and said second primer recognizing a sequence within the foreign DNA consists of 17 to 200 consecutive nucleotides selected from the nucleotide sequence of SEQ ID No 2 from 1 to nucleotide 509.

3. The kit of claim 1, wherein said first primer recognizing the 5' flanking region comprises at its extreme 3' end a nucleotide sequence of at least 17 consecutive nucleotides selected from the nucleotide sequence of SEQ ID No 1 from nucleotide 1 to nucleotide 311, and second primer recognizing a sequence within the foreign DNA comprises at its extreme 3' end a nucleotide sequence of at least 17 consecutive nucleotides selected from the nucleotide sequence of the complement of SEQ ID No 1 from nucleotide 312 to nucleotide 810, or said first primer recognizing the 3' flanking region of A5547-127 comprises at its extreme 3' end a nucleotide sequence of at least 17 consecutive nucleotides selected from the nucleotide sequence of the complement of SEQ ID No 2 from nucleotide 510 to nucleotide 1880, and said primer recognizing a sequence within the foreign DNA comprises at its 3' end at least 17 consecutive nucleotides selected from the nucleotide sequence of SEQ ID No 2 from nucleotide 1 to nucleotide 509.

4. The kit of claim 1, comprising a primer consisting of the sequence of SEQ ID No. 13 and a primer consisting of the sequence of SEQ ID No. 15.

5. A primer pair comprising a first primer having a sequence which, under optimized PCR conditions specifically recognizes a sequence within the 5' flanking region of A5547-127, and a second primer which, under optimized PCR conditions specifically recognizes a sequence within the foreign DNA contiguous with said 5' flanking region, or comprising a first primer which, under optimized PCR conditions specifically recognizes a sequence within the 3' flanking region of A5547-127, and a second primer which, under optimized PCR conditions specifically recognizes a sequence within the foreign DNA contiguous with said 3' flanking region, wherein said 5' flanking region comprises the nucleotide sequence of SEQ ID No 1 from nucleotide 1 to nucleotide 311 and said 3' flanking region having the nucleotide sequence of the complement of SEQ ID No 2 from nucleotide 510 to 1880, said foreign DNA contiguous with said 5' flanking region comprises the nucleotide sequence of the complement of SEQ ID No. 1 from nucleotide 312 to nucleotide 810, and said foreign DNA contiguous with said 3' flanking region comprises the nucleotide sequence of SEQ ID No 2 from nucleotide 1 to nucleotide 509.

6. The primer pair of claim 5, wherein one of said primers consists of a nucleotide sequence of 17 to 200 consecutive nucleotides selected from the nucleotide sequence of SEQ ID No 1 from nucleotide 1 to nucleotide 311 or a nucleotide sequence of 17 to 200 consecutive nucleotides selected from the nucleotide sequence of the complement of SEQ ID No 2 from nucleotide 510 to nucleotide 1880.

7. The primer pair of claim 5, wherein one of said primers comprises at its extreme 3' end a nucleotide sequence of at least 17 consecutive nucleotides selected from the nucleotide sequence of SEQ ID No 1 from nucleotide 1 to nucleotide 311 or a nucleotide sequence of at least 17 consecutive nucleotides selected from the nucleotide sequence of the complement of SEQ ID No 2 from nucleotide 510 to nucleotide 1880.

8. A primer pair comprising a first primer comprising at its extreme 3' end the sequence of SEQ ID No. 13, and a second primer comprising at its extreme 3' end the sequence of SEQ ID No. 15.

9. A kit comprising a specific probe, capable of hybridizing specifically to a specific region of A5547-127, wherein said specific region is a DNA comprising part of the 5' flanking sequence of A5547-127 and the sequence of the foreign DNA contiguous therewith, or is a DNA comprising part of the 3' flanking sequence of A5547-127 and the sequence of the foreign DNA contiguous therewith, wherein said 5' flanking region comprises the nucleotide sequence of SEQ ID No 1 from nucleotide 1 to nucleotide 311, said 3' flanking region comprising the nucleotide sequence of the complement of SEQ ID No 2 from nucleotide 510 to nucleotide 1880, wherein said foreign DNA contiguous with said 5' flanking region comprises the nucleotide sequence of the complement of SEQ ID No. 1 from nucleotide 312 to nucleotide 810, and wherein said foreign DNA contiguous with said 3' flanking region comprises the nucleotide sequence of SEQ ID No 2 from nucleotide 1 to nucleotide 509, or the complement of said sequences, and wherein the sequence of said specific probe has at least 80% sequence identity with SEQ ID No. 1 from nucleotide 260 to 360 or SEQ ID No. 2 from nucleotide 460 to 560, or the complement of said sequences.

10. A specific probe comprising a sequence which has at least 80% sequence identity with a sequence comprising part of the 5' or 3' flanking sequence of A5547-127 and the sequence of the foreign DNA contiguous therewith, or the complement thereof, wherein said 5' flanking region comprises the nucleotide sequence of SEQ ID No 1 from nucleotide 1 to nucleotide 311, said 3' flanking region comprising the nucleotide sequence of the complement of SEQ ID No 2 from nucleotide 510 to nucleotide 1880, wherein said foreign DNA contiguous with said 5' flanking region comprises the nucleotide sequence of the complement of SEQ ID No. 1 from nucleotide 312 to nucleotide 810, and wherein said foreign DNA contiguous with said 3' flanking region comprises the nucleotide sequence of SEQ ID No 2 from nucleotide 1 to nucleotide 509, or the complement of said sequences, wherein the sequence of said specific probe has at least 80% sequence identity with SEQ ID No. 1 from nucleotide 260 to 360 or SEQ ID No. 2 from nucleotide 460 to 560, or the complement of said sequences.

11. A specific probe comprising the nucleotide sequence of SEQ ID No. 1 from nucleotide 260 to 360 or of SEQ ID No. 2 from nucleotide 460 to 560, or the complement of said sequences.

12. A DNA comprising the 5' flanking region of the A5547-127 event and the foreign DNA contiguous therewith, wherein said DNA comprises a sequence of between 50 and 500 bp with at least 80% sequence identity to a DNA comprising the 5' flanking region of the A5547-127 event and the foreign DNA contiguous therewith, said 5' flanking region comprising the nucleotide sequence of SEQ ID No 1 from nucleotide 1 to nucleotide 311, and said foreign DNA contiguous therewith comprising the nucleotide sequence of SEQ ID No. 1 from nucleotide 312 to nucleotide 810; wherein said DNA comprises the sequence of SEQ ID No. 1 from nucleotide 260 to nucleotide 360.

13. A DNA comprising the 3' flanking region of the A5547-127 event and the foreign DNA contiguous therewith, wherein said DNA comprises a sequence with at least 80% sequence identity to a DNA comprising the 3' flanking region of the A5547-127 event and the foreign DNA contiguous therewith, said 3' flanking region comprising the nucleotide sequence of SEQ ID No 2 from nucleotide 510 to nucleotide 1880, and said foreign DNA contiguous therewith comprising the nucleotide sequence of SEQ ID No 2 from nucleotide 1 to nucleotide 509;

wherein said DNA contains the nucleotide sequence of SEQ ID No. 1 from nucleotide position 460 to nucleotide position 560.

14. An isolated DNA comprising a nucleotide sequence with at least 95% sequence identity to the nucleotide sequence of SEQ ID No 1 from nucleotide 260 to nucleotide 360.

15. An isolated DNA comprising a nucleotide sequence with at least 95% sequence identity to the nucleotide sequence of SEQ ID No 2 from nucleotide 460 to nucleotide 560.

16. An isolated DNA comprising the nucleotide sequence of SEQ ID No 1 from nucleotide 260 to nucleotide 360.

17. An isolated DNA comprising the nucleotide sequence of SEQ ID No 2 from nucleotide 460 to nucleotide 560.

* * * * *